US006962922B2

(12) United States Patent
Gaudilliere et al.

(10) Patent No.: US 6,962,922 B2
(45) Date of Patent: Nov. 8, 2005

(54) ALKYNYLATED QUINAZOLINE COMPOUNDS

(75) Inventors: Bernard Gaudilliere, Nanterre (FR); Henri Jacobelli, Paray Vieille Poste (FR); Joseph Armand Picard, Canton, MI (US); Michael William Wilson, Ann Arbor, MI (US)

(73) Assignee: Warner-Lambert Company LLC, Morris Plains, NJ (US)

( * ) Notice: Subject to any disclaimer, the term of this patent is extended or adjusted under 35 U.S.C. 154(b) by 29 days.

(21) Appl. No.: 10/269,197

(22) Filed: Oct. 11, 2002

(65) Prior Publication Data

US 2003/0130278 A1 Jul. 10, 2003

Related U.S. Application Data

(60) Provisional application No. 60/329,181, filed on Oct. 12, 2001, and provisional application No. 60/395,441, filed on Jul. 12, 2002.

(30) Foreign Application Priority Data

Oct. 12, 2001 (WO) ............................... PCT/EP01/11824
Jul. 12, 2002 (WO) ............................... PCT/EP02/08475

(51) Int. Cl.[7] .................... C07D 239/96; C07D 403/06; C07D 401/10; A61K 31/517; A61P 19/02
(52) U.S. Cl. .............................. 514/266.2; 514/266.21; 514/266.23; 514/266.24; 514/266.3; 514/266.31; 433/284; 433/285; 433/287; 433/290
(58) Field of Search .................... 514/266.2, 266.21, 514/266.23, 266.24, 266, 266.3, 266.31; 544/284, 285, 287, 290

(56) References Cited

U.S. PATENT DOCUMENTS

| | | | |
|---|---|---|---|
| 3,655,679 A | 4/1972 | Shen et al. | |
| 4,818,819 A | 4/1989 | Taylor et al. | |
| 4,902,796 A | 2/1990 | Taylor et al. | |
| 5,389,631 A | 2/1995 | Claremon et al. | |
| 5,521,181 A | 5/1996 | Meyer et al. | |
| 5,646,141 A | 7/1997 | Varney et al. | |
| 5,929,097 A | 7/1999 | Levin et al. | |
| 5,948,780 A | 9/1999 | Peterson, Jr. et al. | 514/255 |
| 6,008,243 A | 12/1999 | Bender et al. | 514/422 |
| 6,225,311 B1 | 5/2001 | Levin et al. | |
| 2002/0151555 A1 | 10/2002 | Barvian et al. | 514/256 |
| 2002/0151558 A1 | 10/2002 | Andrianjara et al. | 514/267 |
| 2002/0156061 A1 | 10/2002 | Barvian et al. | 514/183 |
| 2002/0156069 A1 | 10/2002 | Picard et al. | 514/223.2 |
| 2002/0161000 A1 | 10/2002 | Barvian et al. | 514/217.04 |
| 2002/0193377 A1 | 12/2002 | Andrianjara et al. | |
| 2003/0004172 A1 | 1/2003 | Ilarter et al. | |
| 2003/0144274 A1 | 7/2003 | Bunker et al. | |
| 2003/0216402 A1 | 11/2003 | Gaudilliere et al. | |
| 2003/0220355 A1 | 11/2003 | Gaudilliere et al. | |
| 2003/0229103 A1 | 12/2003 | Weithmann et al. | |
| 2004/0006077 A1 | 1/2004 | Gaudilliere et al. | |
| 2004/0038959 A1 | 2/2004 | Bunker et al. | |
| 2004/0044000 A1 | 3/2004 | Bunker et al. | |
| 2004/0063673 A1 | 4/2004 | Johnson | |

FOREIGN PATENT DOCUMENTS

| | | |
|---|---|---|
| EP | 0935963 | 8/1999 |
| EP | 1138680 | 10/2001 |
| JP | 10195063 | 7/1998 |
| WO | 9616046 | 5/1996 |
| WO | 9816514 | 4/1998 |
| WO | WO 00/09485 | 2/2000 |
| WO | 0035906 | 6/2000 |
| WO | 0040561 | 7/2000 |

(Continued)

OTHER PUBLICATIONS

E.C. Taylor, et al., "Pteridines. 51. A New and Unequivocal Route to C–6 Carbon–Substituted Pterins and Pteridines", J. Org. Chem. 1987, 52:3997–4000.

(Continued)

*Primary Examiner*—Thomas C. McKenzie
(74) *Attorney, Agent, or Firm*—Claude F. Purchase, Jr.; Charles W. Ashbrook; Pfizer, Inc.

(57) ABSTRACT

A compound selected from those of formula (I):

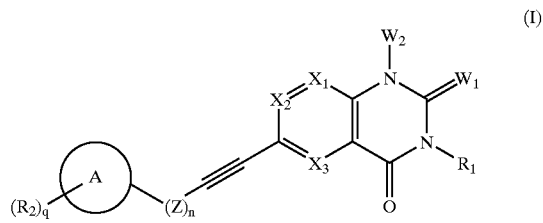

wherein
$W_1$ represents O, S, or —$NR_3$ in which $R_3$ represents hydrogen, alkyl, OH or CN;
$W_2$ represents a group selected from hydrogen, $CF_3$, $NH_2$, monoalkylamino, dialkylamino, alkyl, alkenyl, alkynyl, aryl, arylalkyl, cycloalkylalkyl, heterocycle, these groups being optionally substituted,
or $W_1$ and $W_2$ form together a group of formula —N=$X_4$—$W_3$— as defined in the description,
$X_1$, $X_2$ and $X_3$ represent N or C optionally substituted,
n is 0 to 8,
Z represents —$CR_{12}R_{13}$, wherein $R_{12}$ and $R_{13}$ are as defined in the description,
A represents a ring system,
the groups $R_2$ represent hydrogen or various chemical groups as defined in the description,
q is 0 to 7;
$R_1$ represents hydrogen, alkyl, alkenyl, alkynyl, or a ring system,
and optionally, its optical isomers, N-oxide, and addition salts thereof with a pharmaceutically-acceptable acid or base, and medicinal products containing the same are useful as specific inhibitors of type-13 matrix metalloprotease.

19 Claims, No Drawings

FOREIGN PATENT DOCUMENTS

| WO | 0044716 | 8/2000 |
|---|---|---|
| WO | 0045063 | 8/2000 |
| WO | WO 01/12611 | 2/2001 |
| WO | 0155133 | 8/2001 |
| WO | 0163244 | 8/2001 |
| WO | 0206513 | 1/2002 |
| WO | WO 02/34726 | 5/2002 |
| WO | WO 02/34753 | 5/2002 |
| WO | 02064080 | 8/2002 |
| WO | 02064547 | 8/2002 |
| WO | 02064568 | 8/2002 |
| WO | 02064571 | 8/2002 |
| WO | 02064572 | 8/2002 |
| WO | 02064578 | 8/2002 |
| WO | 02064595 | 8/2002 |
| WO | 02064598 | 8/2002 |
| WO | 02064599 | 8/2002 |
| WO | WO 2003/032999 A1 | 4/2003 |
| WO | WO 2003/076417 A2 | 9/2003 |
| WO | WO 2003/076417 A3 | 9/2003 |
| WO | WO 2004/014378 A1 | 2/2004 |
| WO | WO 2004/014379 A1 | 2/2004 |
| WO | WO 2004/014384 A2 | 2/2004 |
| WO | WO 2004/014921 A1 | 2/2004 |
| WO | WO 2004/000322 A1 | 12/2004 |

OTHER PUBLICATIONS

E.C. Taylor, et al., "Convergent and Efficient Palladium–Effected Synthesis of 5,10–Dideaza–5,6,7,8–tetrahydrofolic Acid (DDATHF)", J. Org. Chem. 1989, 52:3618–3624.

M.G. Natchus, et al., "Development of New Carboxylic Acid–Based MMP Inhibitors Derived from Functionalized Propargylglycines", Journal of Medicinal Chemistry 2001, 44(7):1060–1071.

Derwent Publication Lt. Abstract No. 2001–514548; XP002213435.

A.B. Dyatkin et al., "The Solid Phase Synthesis of Complex Propargylamines Using the Combination of Sonogashira and Mannich Reactions", Tetrahedron Letters, Elsevier Science Publishers, Amsterdam, NL 1998, 39(22)3647–3650.

John Montana & Andrew Baxter, "The design of selective non–substrate–based matrix metalloproteinase inhibitors", Current Opinion in Drug Discovery & Development 2000, 3(4):353–361.

Clark et al., "Matrix metalloproteinase inhibitors in the treatment of arthritis", Current Opinion in Anti–inflammatory & Immunomodulatory Investigational Drugs 2000, 2(1):16–25.

Chen et al., "Structure–Based Design of a Novel, Potent, and Selective Inhibitor for MMP–13 Utilizing NMR Spectroscopy and Computer–Aided Molecular Design", J. Am. Chem. Soc. 2000, 122:9648–9664.

Wernicke, et al., "Cloning of Collagenase 3 from the Synovial Membrane and Its Expression in Rheumatoid Arthritis and Osteoarthritis". J. Rheum., 1996; 23: 590–595.

Reboul, et al., "The New Collagenase–3. Is Expressed and Synthesized by Human Chondrocytes but not by Synoviocytes", J. Clin. Invest., 1996; 97: 2011–2019.

Freemont, et al., "In situ zymographic localisation of type II collagen degrading activity in osteoarthritic human articular cartilage", Ann. Rheum. Dis., 1999; 58: 357–365.

U.S. Appl. No. 10/071,032, filed Feb. 8, 2002, Dyer et al.

U.S. Appl. No. 10/634,489, filed Aug. 5, 2003, Roark.

Lisa A. Neuhold, et al., "Postnatal expression in hyaline cartilate of constitutively active human collagenase–3 (MMP–13) induces osteoarthritis in mice", J. Clin. Invest., 2001: 107(1): 35–44.

Leif Dahlberg, et al., "Selective enhancement of collagenase–mediated cleavage of resident type II collagen in cultured osteoarthritic cartilage and arrest with a synthetic inhibitor that spares collagenase 1 (Matrix Metalloproteinase1)", Arthritis & Rheum., 2000: 43(3): 673–682.

R. Clark Billinghurst, et al., "Comparison of the degradation of type II collagen and proteoglycan in nasal articular cartilages induced by interleukin–1 and the selective inhibition of type II collagen cleavage by collagenase", Arthritis & Rheum., 2000; 43(3): 664–672.

Peter G. Mitchell, et al., "Cloning, Expression, and Type II Collagenolytic Activity of Matrix Metalloproteinase–13 from Human Osteoarthritic Cartilage", J. Clin. Invest., 1996; 97(3): 761–768.

R. Clark Billinghurst, et al., "Enhanced Cleavage of Type II Collagen by Collagenases in Osteoarthritic Articular Cartilage", J. Clin. Invest., 1997; 99(7); 1534–1545.

Nedjeljko Kujundzic, et al., "Synthesis of 8–Methyl–1,2,3, 4–tetrahydropyrido–[3,4–d]pyrimidine–2,4–diones". Coratica Chemica Acta, 1991: 64(4): 599–606.

Kosaku Hirota, et al., "Novel Synthesis of Pyrido[3,4–Id] pyrimidines, Pyrido[2,3–d]–pyrimidines, and Quinazolines Via Palladium–catalyazed Oxidative Coupling", Heterocycles, 1994; 37(1): 563–570.

ALKYNYLATED QUINAZOLINE COMPOUNDS

CROSS-REFERENCE TO RELATED APPLICATIONS

This application claims benefit of priority from PCT International patent application nos. PCT/EP01/11824, filed Oct. 12, 2001, and PCT/EP02/08475, filed Jul. 12, 2002, and U.S. provisional patent application nos. 60/329,181, filed Oct. 12, 2001, and 60/395,441, filed July 12, 2002.

FIELD OF THE INVENTION

The present invention relates to novel alkynylated fused ring pyrimidine compounds which are useful for preparing medicinal products for treating complaints involving a therapy with a matrix metalloprotease-13 (MMP-13) inhibitor. These medicinal products are useful in particular for treating certain inflammatory conditions such as rheumatoid arthritis or osteoarthritis, as well as certain proliferative conditions such as cancers.

TECHNOLOGICAL BACKGROUND OF THE INVENTION

Matrix metalloproteases (MMPs) are enzymes which are involved in the renewal of extracellular matrix tissue, such as cartilage, tendons and joints. MMPs bring about the destruction of the extracellular matrix tissue, which is compensated for, in a non-pathological physiological state, by its simultaneous regeneration.

Under normal physiological conditions, the activity of these extremely aggressive peptidases is controlled by specialized proteins, which inhibit MMPs, such as the tissue inhibitors of metalloprotease (TIMPs).

Local equilibrium of the activities of MMPs and of TIMPs is critical for the renewal of the extracellular matrix. Modifications of this equilibrium, which result in an excess of active MMPs, relative to their inhibitor, induce a pathological destruction of cartilage, which is observed in particular in rheumatoid arthritis and in osteoarthritis.

In pathological situations, an irreversible degradation of articular cartilage takes place, as is the case in rheumatic diseases such as rheumatoid arthritis or osteoarthritis. In these pathologies, the cartilage degradation process predominates, leading to a destruction of the tissue and resulting in a loss of function.

At least twenty different matrix metalloproteases have been identified to date and are subdivided into four groups, the collagenases, the gelatinases, the stromelysins and the membrane-type MMPs (MT-MMPs), respectively.

Matrix metalloprotease-13 (MMP-13) is a collagenase-type MMP which constitutes the predominant collagenase observed during osteoarthritis, in the course of which pathology the chondrocyte directs the destruction of cartilage.

There is a need in the prior art for novel MMP inhibitors, more particularly for MMP-13 inhibitors, in order to prevent and/or correct the imbalance in the renewal of extracellular matrix tissue, such as arthritis, rheumatoid arthritis, osteoarthritis, osteoporosis, periodontal diseases, inflammatory bowel disease, psoriasis, multiple sclerosis, cardiac insufficiency, atherosclerosis, asthma, chronic obstructive pulmonary diseases (COPD), age-related macular degeneration (ARMD) and cancer.

MMP-inhibitor compounds are known. Most of these MMP-inhibitors are not selective for a single MMP, such as those described by Montana and Baxter (2000) or by Clark et al. (2000).

There is also a need in the prior art for novel inhibitors that are active on matrix metalloprotease-13, in order to enrich the therapeutic arsenal that can be used for treating pathologies associated with the destruction of the extracellular matrix and with cancer.

PRIOR ART DESCRIPTION

The patent application WO9826664 describes quinazolinone compounds which are used as new antifungic compounds. The U.S. Pat. No. 5,389,631 describes new dioxoquinazoline and dioxobenzodiazepine amino acid derivatives which are analogs as fibrinogen receptor antagonists and can be used in the treatment of pathologies wherein inhibition of the fibrinogen of blood and inhibition of the aggregation of blood platelets are involved. The U.S. Pat. Nos. 4,818,819 and 4,902,796 describes a process for the preparation of some alkenyl derivatives of pyrido[2,3-d] pyrimidine, which are chemicals intermediates for the preparation of antineoplastic agents.

The compounds of the present application are novel and represent powerful inhibitors of MMP-13. They are consequently of use in the treatment of rheumatoid arthritis, osteoarthritis, osteoporosis, periodontal diseases, inflammatory bowel disease, psoriasis, multiple sclerosis, cardiac insufficiency, atherosclerosis, asthma, chronic obstructive pulmonary diseases (COPDs), age-related degeneration (ARMD) and cancer.

SUMMARY OF THE INVENTION

The applicant has identified novel alkynylated fused ring pyrimidine compounds that are matrix metalloprotease inhibitors, and more specifically compounds that are selective MMP-13 inhibitors. More specifically, the present invention relates to compounds of formula (I):

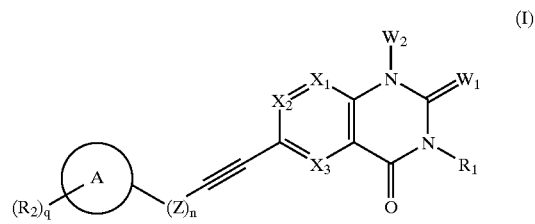

wherein
$W_1$ represents an oxygen atom, a sulfur atom, or a —$NR_3$ group in which $R_3$ represents hydrogen atom, ($C_1$–$C_6$) alkyl, hydroxyl or cyano,
$W_2$ represents a group selected from:
  hydrogen atom, trifluoromethyl, amino, mono($C_1$–$C_6$) alkylamino, di($C_1$–$C_6$)alkylamino,
  ($C_1$–$C_6$)alkyl, ($C_2$–$C_6$)alkenyl, ($C_2$–$C_6$)alkynyl, aryl, aryl ($C_1$–$C_6$)alkyl, cycloalkyl($C_1$–$C_6$)alkyl, 5- or 6-membered monocycle heteroaryl, and 5- or 6-membered monocycle heterocycloalkyl, each of these groups being optionally substituted by one to four groups, which may be identical or different independently of each other, selected from halogen, amino, mono($C_1$–$C_6$)alkylamino, di($C_1$–$C_6$)alkylamino, cyano, trihalogeno($C_1$–$C_6$)alkyl, ($C_1$–$C_7$)acyl, —C(=O)$OR_4$, —$OR_4$ and —$SR_4$, wherein $R_4$ represents a hydrogen atom or a ($C_1$–$C_6$)alkyl group,
or $W_1$ and $W_2$ form together a group of formula N—$X_4$=$W_3$ (in which the nitrogen atom is bound in place of the group $W_1$ and the group $W_3$ is bound in place of the group $W_2$) wherein:
$W_3$ represents a nitrogen atom or a group —$CR_5$ in which $R_5$ is selected from:
a hydrogen atom,
—$OR_6$, —$SR_6$ in which $R_6$ is selected from hydrogen, ($C_1$–$C_6$)alkyl and aryl($C_1$–$C_6$)alkyl;
($C_1$–$C_6$)alkyl, cycloalkyl, aryl, aryl($C_1$–$C_6$)alkyl, heteroaryl, and heterocycloalkyl, each of these groups being optionally substituted by a group selected from —$(CH_2)_p$—OH and —$(CH_2)_p$—$NH_2$, wherein p is an integer from 0 to 4 inclusive,
$X_4$ represents a nitrogen atom or a group —$CR_7$ in which $R_7$ is selected from hydrogen, —$NR_8R_9$, —$OR_8$, —$SR_8$, ($C_1$–$C_6$)alkyl, cycloalkyl, aryl, aryl($C_1$–$C_{10}$)alkyl, heteroaryl, and heterocycloalkyl,
each of these groups being optionally substituted by a group selected from —$(CH_2)_p$—OH and —$(CH_2)_p$—$NH_2$, wherein p is as defined hereinbefore,
and in which $R_8$ and $R_9$, identical or different independently of each other, are selected from hydrogen, ($C_1$–$C_6$)alkyl and aryl($C_1$–$C_6$)alkyl,
$X_1$, $X_2$ and $X_3$, identical or different independently of each other, represent a nitrogen atom or a carbon atom, the said carbon atom being optionally substituted by one group selected from:
($C_1$–$C_6$)alkyl, hydroxyl, ($C_1$–$C_6$)alkoxy, halogen, trifluoromethyl, cyano, nitro,
—$S(O)_{n1}R_4$ wherein $n_1$ represents an integer from 0 to 2 inclusive and $R_4$ represents an hydrogen atom or a ($C_1$–$C_6$)alkyl group,
and —$NR_{10}R_{11}$ wherein:
$R_{10}$ and $R_{11}$, which may be identical or different independently of each other, represent a group selected from hydrogen, ($C_1$–$C_6$)alkyl, hydroxy($C_1$–$C_6$)alkyl, and aryl($C_1$–$C_6$)alkyl,
or $R_{10}$ and $R_{11}$ form together with the nitrogen atom to which there are bound, a 5- or 6-ring members which can optionally contain a second hetero atom selected from nitrogen and oxygen, and which can be optionally substituted by a ($C_1$–$C_6$)alkyl group,
with the proviso that not more than two of the groups $X_1$, $X_2$ and $X_3$ simultaneously represent a nitrogen atom,
n is an integer from 0 to 8 inclusive,
Z represents —$CR_{12}R_{13}$, wherein $R_{12}$ and $R_{13}$, identical or different independently of each other, represent a group selected from hydrogen, ($C_1$–$C_6$)alkyl, trihalogeno($C_1$–$C_6$)alkyl, halogen, amino, mono($C_1$–$C_6$)alkylamino, di($C_1$–$C_6$)alkylamino, —$OR_4$, —$SR_4$, —$C(=O)OR_4$, $R_4$ being as defined hereinbefore, or —$CR_{12}R_{13}$ form together a carbonyl group, and
wherein when n is greater than or equal to 2, the hydrocarbon chain Z optionally contains one or two isolated or conjugated multiple bonds,
and/or wherein when n is greater than or equal to 2 one of said —$CR_{12}R_{13}$ may be replaced with a group selected from oxygen, $S(O)_{n2}$ in which n2 represents an integer from 0 to 2 inclusive, —NH and —$N(C_1$–$C_6$)alkyl,
A represents a group selected from aryl, heteroaryl, cycloalkyl, and heterocycloalkyl, these groups being a 5- or 6-membered monocycle, or bicycle itself composed of two 5- or 6-membered monocycles,
the groups $R_2$, which may be identical or different independently of each other, are selected from hydrogen, ($C_1$–$C_6$)alkyl, halogen, cyano, nitro, trihalogeno($C_1$–$C_6$)alkyl, —$NR_{10}R_{11}$, —$OR_{14}$, —$SR_{14}$, —$SOR_{14}$, —$SO_2R_{14}$,
($C_1$–$C_7$)acyl, —$(CH_2)_kNR_{10}R_{11}$, —$X_5(CH_2)_kNR_{10}OR_{11}$, —$(CH_2)_kSO_2NR_{14}R_{15}$, —$X_5(CH_2)_kC(=O)OR_{14}$, —$(CH_2)_kC(=O)OR_{14}$, —$X_5(CH_2)_kC(=O)NR_{14}R_{15}$, —$(CH_2)_kC(=O)NR_{14}R_{15}$, —$X_6$—$R_{16}$ and tri($C_1$–$C_6$)alkyl-Si—O— in which each alkyl is identical or different independently of each other, and in which:
$X_5$ represents an oxygen atom, a sulfur atom, a —NH group, or a —$N(C_1$–$C_6$)alkyl group,
k is an integer from 0 to 3 inclusive,
$R_{10}$ and $R_{11}$ are as defined hereinbefore,
$R_{14}$ and $R_{15}$, identical or different independently of each other, represent hydrogen or ($C_1$–$C_6$)alkyl,
$X_6$ represents a single bond, —$CH_2$—, an oxygen atom or a sulfur atom which is optionally substituted with one or two oxygen atoms,
$R_{16}$ represents a group selected from aryl, heteroaryl, heterocycloalkyl, and cycloalkyl, each of these groups being optionally substituted by one to four groups, which may be identical or different independently of each other, selected from ($C_1$–$C_6$)alkyl, halogen, trihalogeno($C_1$–$C_6$)alkyl, hydroxyl, ($C_1$–$C_6$)alkoxy, mercapto, ($C_1$–$C_6$)alkylthio, amino, mono($C_1$–$C_6$)alkylamino, and di($C_1$–$C_6$)alkylamino,
q is an integer from 0 to 7 inclusive,
$R_1$ represents a group selected from:
hydrogen, ($C_1$–$C_6$)alkyl, ($C_2$–$C_6$)alkenyl, and ($C_2$–$C_6$)alkynyl, the groups alkyl, alkenyl and alkynyl being optionally substituted by one to three groups, which may be identical or different independently of each other, selected from amino, mono($C_1$–$C_6$)alkylamino, di($C_1$–$C_6$)alkylamino, cyano, trihalogeno($C_1$–$C_6$)alkyl, —$C(=O)OR_4$, —$OR_4$, —$SR_4$, in which $R_4$ is as defined hereinbefore,
and the group of formula:

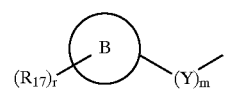

in which:
m is an integer from 0 to 8 inclusive,
Y represents —$CR_{18}R_{19}$, wherein $R_{18}$ and $R_{19}$, identical or different independently of each other, represent a group selected from hydrogen, ($C_1$–$C_6$)alkyl, phenyl, trihalogeno($C_1$–$C_6$)alkyl, halogen, amino, mono($C_1$–$C_6$)alkylamino, di($C_1$–$C_6$)alkylamino, —$OR_4$, —$SR_4$ and —$C(=O)OR_4$ wherein $R_4$ is as defined hereinbefore, and
wherein when m is greater than or equal to 2, the hydrocarbon chain Y optionally contains one or two isolated or conjugated multiple bonds,
and/or wherein when m is greater than or equal to 2, one of said —$CR_{18}R_{19}$ may be replaced with a group selected from oxygen, —$S(O)_{n3}$ wherein n3 is an integer from 0 to 2 inclusive, —NH— and —$N(C_1$–$C_6$)alkyl,
B represents a group selected from aryl, heteroaryl, cycloalkyl, and heterocycloalkyl, these groups being a 5- or 6-membered monocycle, or bicycle itself composed of two 5- or 6-membered monocycles,
r is an integer from 0 to 7 inclusive,
the group(s) $R_{17}$, which may be identical or different independently of each other, are selected from hydrogen, ($C_1$–$C_6$)alkyl, halogen, cyano, nitro, trihalogeno($C_1$–$C_6$)alkyl, —$NR_{10}R_{11}$, —$OR_{14}$, —$SR_{14}$, —$SOR_{14}$, —$SO_2R_{14}$, ($C_1$–$C_7$)acyl, —$(CH_2)_k NR_{10}R_{11}$, —$(CH_2)_k$—$OR_{14}$, —$(CH_2)_k$—$SR_{14}$, —$(CH_2)_k$—$SOR_{14}$, —$(CH_2)_k$—$SO_2R_{14}$, —$X_5(CH_2)_k NR_{10}R_{11}$, —$(CH_2)_k SO_2NR_{14}R_{15}$, —$X_5(CH_2)_k C(=O)OR_{14}$, —$(CH_2)_k C(=O)OR_{14}$, —$X_5(CH_2)_k C(=O)NR_{10}R_{11}$, —$(CH_2)_k C(=O)NR_{10}R_{11}$, —$X_6$—$R_{16}$, and —$(CH_2)_k$—$C(O)$—$OR_{20}$, in which:

$X_5$, k, $R_{10}$, $R_{11}$, $R_{14}$, $R_{15}$, $X_6$ and $R_{16}$ are as defined hereinbefore, and $R_{20}$ represents a group selected from —T—$OR_{14}$, —T—$NR_{10}R_{11}$, —T—$C(O)OR_{14}$, —T—$C(O)NR_{10}R_{11}$ in which T represents a linear or branched ($C_1$–$C_6$)alkylene chain and $R_{14}$, $R_{10}$, and $R_{11}$ are as defined hereinbefore, and optionally, their optical isomers, N-oxides, and addition salts thereof with a pharmaceutically-acceptable acid or base, with the proviso that when $W_1$ represents —$NR_3$, $W_2$ represents hydrogen atom, $X_1$ and $X_2$ represent each a —CH group, $X_3$ represents nitrogen atom, n is equal to zero, A represents a phenyl group, q is equal to one, $R_1$ represents hydrogen atom, and $R_2$ represents a group —$(CH_2)_k$—$CO_2R_{14}$ bound on the para position of the phenyl ring, then k is an integer from 1 to 6, and also with the proviso that compounds of formula (I) is not 2-amino-6-phenylethynyl-3H-pteridin-4-one.

According to a first embodiment, the invention relates to compounds of formula (I) wherein:

$W_1$ represents an oxygen atom, a sulfur atom, or a —$NR_3$ group in which $R_3$ represents hydrogen atom, ($C_1$–$C_6$) alkyl, hydroxyl or cyano, $W_2$ represents a group selected from:
hydrogen atom, trifluoromethyl, amino, mono($C_1$–$C_6$) alkylamino, di($C_1$–$C_6$)alkylamino,
($C_1$–$C_6$)alkyl, ($C_2$–$C_6$)alkenyl, ($C_2$–$C_6$)alkynyl, aryl, aryl($C_1$–$C_6$)alkyl, cycloalkyl($C_1$–$C_6$)alkyl, 5- or 6-membered monocycle heteroaryl, and 5- or 6-membered monocycle heterocycloalkyl, each of these groups being optionally substituted by one to four groups, which may be identical or different independently of each other, selected from halogen, amino, mono($C_1$–$C_6$)alkylamino, di($C_1$–$C_6$)alkylamino, cyano, trihalogeno($C_1$–$C_6$)alkyl, ($C_1$–$C_7$)acyl, —$C(=O)OR_4$, —$OR_4$ and —$SR_4$, wherein $R_4$ represents a hydrogen atom or a ($C_1$–$C_6$)alkyl group, and $X_1$, $X_2$, $X_3$, $R_1$, $R_2$, A, Z, n and q are as defined hereinbefore.

According to a second embodiment, the invention relates to compounds of formula (I) corresponding to formula (IA):

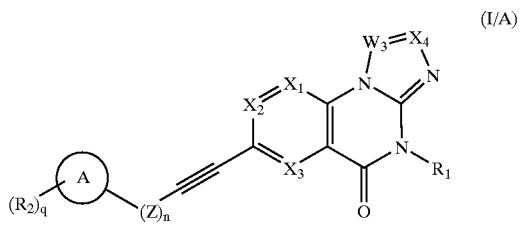

(I/A)

wherein:
$W_3$ represents a nitrogen atom or a group —$CR_5$ in which $R_5$ is selected from:
a hydrogen atom,
—$OR_6$, —$SR_6$ in which $R_6$ is selected from hydrogen, ($C_1$–$C_6$)alkyl and aryl($C_1$–$C_6$)alkyl;

($C_1$–$C_6$)alkyl, cycloalkyl, aryl, aryl($C_1$–$C_6$)alkyl, heteroaryl, and heterocycloalkyl, each of these groups being optionally substituted by a group selected from —$(CH_2)_p$—OH and —$(CH_2)_p$—$NH_2$, wherein p is an integer from 0 to 4 inclusive, $X_4$ represents a nitrogen atom or a group —$CR_7$ in which $R_7$ is selected from hydrogen, —$NR_8R_9$, —$OR_8$, —$SR_8$, ($C_1$–$C_6$)alkyl, cycloalkyl, aryl, aryl($C_1$–$C_{10}$) alkyl, heteroaryl, and heterocycloalkyl,
each of these groups being optionally substituted by a group selected from —$(CH_2)_p$—OH and —$(CH_2)_p$—$NH_2$, wherein p is as defined hereinbefore,
and in which $R_8$ and $R_9$, identical or different independently of each other, are selected from hydrogen, ($C_1$–$C_6$)alkyl and aryl($C_1$–$C_6$)alkyl, and $X_1$, $X_2$, $X_3$, $R_1$, $R_2$, A, Z, n and q are as defined in formula (I).

The invention relates particularly to the compounds of formula (I) in which:
$W_2$ represents a group selected from hydrogen atom, ($C_1$–$C_6$)alkyl, aryl($C_1$–$C_6$)alkyl and ($C_3$–$C_6$)cycloalkyl ($C_1$–$C_6$)alkyl,
$W_1$ represents an oxygen atom or a sulfur atom,
$X_1$ represents a —CH group,
$X_2$ represents a —CH group or a nitrogen atom,
$X_3$ represents a —CH group,
and $R_1$, $R_2$, A, Z, n and q are as defined in formula (I).

The invention relates also particularly to the compounds of formula (I) in which:
$W_2$ represents a group selected from hydrogen atom, amino, mono($C_1$–$C_6$)alkylamino, di($C_1$–$C_6$)alkylamino, ($C_1$–$C_6$) alkyl, ($C_2$–$C_6$)alkenyl, ($C_2$–$C_6$)alkynyl, aryl, aryl($C_1$–$C_6$) alkyl, and ($C_3$–$C_6$)cycloalkyl($C_1$–$C_6$)alkyl,
$W_1$ represents an oxygen atom or a sulfur atom,
$X_1$ represents a nitrogen atom or a —CH group
$X_2$ represents a —CH group,
$X_3$ represents a —CH group,
and $R_1$, $R_2$, A, Z, n and q are as defined in formula (I).

In a particular embodiment the invention relates to the compounds of formula (IA):

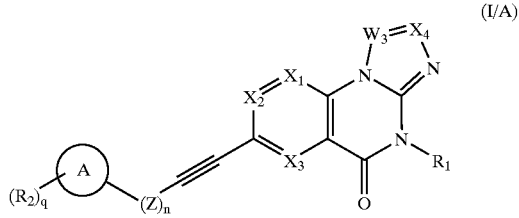

(I/A)

wherein:
$W_3$ represents —$CR_5$ wherein $R_5$ represents a hydrogen atom or a methyl group,
$X_4$ represents a nitrogen atom or —$CR_7$ wherein $R_7$ represents a hydrogen atom or a methyl group,
n is an integer from 1 to 4 inclusive,
and $X_1$, $X_2$, $X_3$, $R_1$, $R_2$, A, Z and q are as defined in the formula (I).

In another embodiment, the invention relates particularly to the compounds of formula (I) in which:
$W_2$ represents a group ($C_1$–$C_6$)alkyl,
$W_1$ represents an oxygen atom,
$X_1$ represents a —CH— group,
$X_2$ represents a —CH— group,
$X_3$ represents a —CH— group,
and $R_1$, $R_2$, A, Z, n and q are as defined in formula (I).

The invention also relates to the compounds of formula (I) in which:

A represents a group selected from phenyl, pyridyl, thienyl, imidazolyl, furyl, benzodioxolyl, benzodioxinyl, benzothienyl, benzofuryl, benzo-1,2,5-thiadiazolyl, benzo-1,2,5-oxadiazolyl and indolyl, q is an integer from 0 to 4 inclusive, the group(s) $R_2$, which may be identical or different, are selected from hydrogen, $(C_1-C_6)$alkyl, halogen, cyano, nitro, trihalogeno$(C_1-C_6)$alkyl, —$NR_{14}R_{15}$, —$OR_{14}$, —$SO_2R_{14}$, —$(CH_2)_kSO_2NR_{14}R_{15}$, —$X_5(CH_2)_kC(=O)OR_{14}$, —$(CH_2)_kC(=O)OR_{14}$, —$X_5(CH_2)_kC(=O)NR_{14}R_{15}$, —$(CH_2)_kC(=O)NR_{14}R_{15}$ and —$X_6$—$R_{16}$ in which:

$X_5$ represents an oxygen atom, a sulfur atom, or a —NH group, k is an integer from 0 and 3 inclusive, $R_{14}$ and $R_{15}$ identical or different, independently of each other, represent hydrogen or $(C_1-C_6)$alkyl, $X_6$ represents an oxygen atom, $R_{16}$ represents a phenyl group which is optionally substituted with one or more groups, which may be identical or different, independently of each other, selected from $(C_1-C_6)$alkyl, halogen, and hydroxyl, and $W_1$, $W_2$, $X_1$, $X_2$, $X_3$, $R_1$, Z and n are as defined in formula (I).

The invention also relates to the compounds of formula (I) in which:

A represents a group selected from phenyl, pyridinyl, thienyl, imidazolyl, furyl, and benzodioxolyl, q is an integer from 0 to 4 inclusive, the group(s) $R_2$, which may be identical or different independently of each other, are selected from hydrogen, $(C_1-C_6)$alkyl, halogen, cyano, nitro, trihalogeno$(C_1-C_6)$alkyl, —$NR_{14}R_{15}$, —$OR_{14}$, —$SO_2R_{14}$, —$(CH_2)_kSO_2NR_{14}R_{15}$, —$X_5(CH_2)_kC(=O)OR_{14}$, —$(CH_2)_kC(=O)OR_{14}$, —$X_5(CH_2)_kC(=O)NR_{14}R_{15}$, and —$(CH_2)_kC(=O)NR_{14}R_{15}$ in which:

$X_5$ represents an oxygen atom, a sulfur atom, or a —NH group, k is an integer from 0 and 3 inclusive, $R_{14}$ and $R_{15}$ identical or different, independently of each other, represent hydrogen or $(C_1-C_6)$alkyl, and $W_1$, $W_2$, $X_1$, $X_2$, $X_3$, $R_1$, Z and n are as defined in formula (I).

The invention also relates to the compounds of formula (I) in which:

A represents a group selected from phenyl, imidazolyl, 1H-[1,2,3]triazolyl, and 1H-[1,2,4]triazolyl, q is an integer from 0 to 2 inclusive, the group(s) $R_2$, which may be identical or different, independently of each other, are selected from hydrogen, —$OR_{14}$, —$X_6$—$R_{16}$, and tri$(C_1-C_6)$alkyl-Si—O— in which each alkyl is identical or different independently of each other, in which:

$R_{14}$ represents hydrogen or $(C_1-C_6)$alkyl, $X_6$ represents a single bond, $R_{16}$ represents a phenyl group and $W_1$, $W_2$, $X_1$, $X_2$, $X_3$, $R_1$, Z and n are as defined in formula (I).

The substituent A that is preferred according to the invention is the phenyl group or the 1-imidazolyl group optionally substituted by one group $R_2$ as defined in the compound of the formula (I).

The substituent A that is preferred according to a specific embodiment of the invention is the phenyl group optionally substituted by one group $R_2$ as defined in the compound of the formula (I).

Especially preferred compounds of the invention are compounds of formula (I) wherein A, $R_2$ and q, took together, represent a para-methoxyphenyl group.

Preferred compounds of the invention are those compounds of formula (I) wherein n is equal to one.

Advantageously, preferred compounds of the invention are those compounds of formula (I) wherein Z represents a group —$CR_{12}R_{13}$ in which $R_{12}$ and $R_{13}$ represent each a hydrogen atom.

The invention also relates to the compounds of formula (I) in which $R_1$ represents hydrogen, $(C_1-C_6)$alkyl or the group of formula:

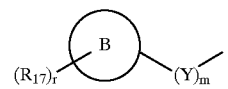

in which:

m is an integer from 0 to 3 inclusive,

Y represents —$CR_{18}R_{19}$, wherein $R_{18}$ and $R_{19}$, identical or different independently of each other, represent a group selected from hydrogen, $(C_1-C_6)$alkyl, and phenyl, and wherein when m is greater than or equal to 2, the hydrocarbon chain Y optionally contains one multiple bonds, and/or wherein when m is greater than or equal to 2, one of said —$CR_{18}R_{19}$ may be replaced with a group selected from oxygen, —$S(O)_{n3}$ wherein n3 is an integer from 0 to 2 inclusive, and —NH—, B represents a group selected from phenyl, pyridinyl, thienyl, imidazolyl, furyl, benzodioxolyl, benzodioxinyl, benzothienyl, benzofuryl, benzo-1,2,5-thiadiazolyl, benzo-1,2,5-oxadiazolyl, naphtyl and indolyl, r is an integer from 0 to 3 inclusive, the group(s) $R_{17}$ which may be identical or different, independently of each other, are selected from hydrogen, $(C_1-C_6)$alkyl, halogen, cyano, nitro, trihalogeno$(C_1-C_6)$alkyl, —$NR_{14}R_{15}$, —$OR_{14}$, —$SO_2R_{14}$, —$(CH_2)_kSO_2NR_{14}R_{15}$, —$X_5(CH_2)_kC(=O)OR_{14}$, —$(CH_2)_kC(=O)OR_{14}$, —$X_5(CH_2)_kC(=O)NR_{14}R_{15}$, —$(CH_2)_kC(=O)NR_{14}R_{15}$ wherein:

k is an integer from 0 to 3 inclusive, $X_5$ represents an oxygen atom, a sulfur atom, or a group —NH—, $R_{14}$ and $R_{15}$, identical or different independently of each other, represent a hydrogen atom or a $(C_1-C_6)$ alkyl group, and $W_1$, $W_2$, $X_1$, $X_2$, $X_3$, $R_2$, Z, n and q are as defined in formula (I).

The invention relates also to the compound of formula (I) in which $R_1$ represents a group of formula:

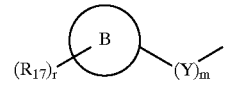

in which:

m is an integer from 0 to 3 inclusive,

Y represents —$CR_{18}R_{19}$, wherein $R_{18}$ and $R_{19}$, identical or different independently of each other, represent a group selected from hydrogen and methyl, and wherein when m is greater than or equal to 2, the hydrocarbon chain Y optionally contains one double bonds, and/or wherein when m is greater than or equal to 2, one of said —$CR_{18}R_{19}$ may be replaced with a group selected from oxygen, —$S(O)_{n3}$ wherein n3 is an integer from 0 to 2 inclusive, and —NH—, B represents a group selected from phenyl, pyridinyl, thienyl, imidazolyl, furyl, and benzodioxolyl, r is an integer from 0 to 3 inclusive, the group(s) $R_{17}$ which may be identical or different, independently of each other, are selected from hydrogen, ($C_1$–$C_6$)alkyl, halogen, cyano, nitro, trihalogeno($C_1$–$C_6$)alkyl, —$NR_{14}R_{15}$, —$OR_{14}$, —$SO_2R_{14}$, —$(CH_2)_kSO_2NR_{14}R_{15}$, —$X_5(CH_2)_kC(=O)OR_{14}$, $(CH_2)_kC(=O)OR_{14}$, —$X_5(CH_2)_kC(=O)NR_{14}R_{15}$, —$(CH_2)_kC(=O)NR_{14}R_{15}$ wherein:

k is an integer from 0 to 3 inclusive, $X_5$ represents an oxygen atom, a sulfur atom, or a group —NH, $R_{14}$ and $R_{15}$, identical or different independently of each other, represent a hydrogen atom or a ($C_1$–$C_6$) alkyl group, and $W_1$, $W_2$, $X_1$, $X_2$, $X_3$, $R_2$, Z, n and q are as defined in formula (I).

Still other preferred compounds of the invention are compounds of formula (I) wherein $W_2$ represents an oxygen atom, $W_1$ represents a linear or branched ($C_1$–$C_6$)alkyl group and $R_1$ represents a group of formula:

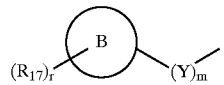

in which Y, B, $R_{17}$, m and r are as defined in the compound of formula (I).

The substituent $R_1$ that is preferred according to the invention is the group of formula:

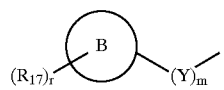

in which m is equal to one, Y represents a methylene group, B represents a phenyl group which is optionally substituted with one group $R_{17}$ which represents a group $(CH_2)_k$—C(=O)$OR_{14}$ in which k and $R_{14}$ are as defined in the compound of formula (I).

Still other preferred compounds of the invention are compounds of formula (IA) wherein $W_1$ and $W_2$ form together a group or formula N—$X_4$=$W_3$ wherein $W_3$ represents a group —$CR_5$ in which $R_5$ is an hydrogen atom, $X_4$ represents an nitrogen atom and $R_1$ represents a group of formula:

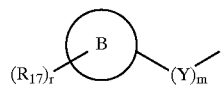

in which Y, B, $R_{17}$, m and r are as defined in the compound of formula (IA).

Still other preferred compounds of the invention are compounds of formula (IA) wherein $R_1$ represents a group of formula:

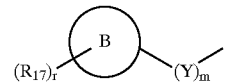

in which m is equal to one, Y represents a methylene group, B represents a phenyl group which is optionally substituted with one group $R_{17}$ which represents a group —$(CH_2)_k$—C(=O)$OR_{14}$ in which k and $R_{14}$ are as defined in the compound of formula (IA).

The substituent $R_1$ that is preferred according to the invention is the group of formula:

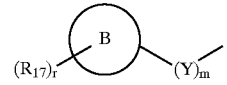

in which m is equal to one, Y represents a methylene group, B represents a phenyl group, r is equal to one, and $R_{17}$ represents a group selected from —$(CH_2)_k$—C(=O)$OR_{14}$, —$(CH_2)_k$—$OR_{14}$, —$(CH_2)_kC(=O)NR_{10}R_{11}$, —$(CH_2)_k$—C(O)—$OR_{20}$, in which:

k, $R_{10}$, $R_{11}$, and $R_{14}$ are as defined in the compound of formula (I), and $R_{20}$ represents a group —T—$NR_{10}R_{11}$, in which T represents a linear or branched ($C_2$–$C_4$)alkylene chain and $R_{10}$, and $R_{11}$ are as defined in the compound of formula (I).

More particularly, the invention related to the following compounds of formula (I):

methyl 4-{6-[3-(4-methoxyphenyl)-prop-1-ynyl]-1-methyl-2,4-dioxo-1,4-dihydro-2H-quinazolin-3-ylmethyl}-benzoate, 4-[1-methyl-2,4-dioxo-6-(3-phenyl-prop-1-ynyl)-1,4-dihydro-2H-quinazolin-3-ylmethyl]-benzoic acid, 4-{6-[3-(4-methoxy-phenyl)-prop-1-ynyl]-1-methyl-2,4-dioxo-1,4-dihydro-2H-quinazolin-3-ylmethyl}-benzoic acid, 4-[1-methyl-2,4-dioxo-6-(3-phenyl-prop-1-ynyl)-1,4-dihydro-2H-pyrido[3,4-d]pyrimidin-3-ylmethyl]-benzoic acid, 4-{6-[3-(4-methoxy-phenyl)-prop-1-ynyl]-1-methyl-2,4-dioxo-1,4-dihydro-2H-pyrido[3,4-d]pyrimidin-3-ylmethyl}-benzoic acid, 4-benzyl-7-(3-phenyl-prop-1-ynyl)-4H-[1,2,4]triazolo[4,3-a]quinazolin-5-one, 4-benzyl-7-[(4-methoxyphenyl)-prop-1-ynyl]-4H-[1,2,4]-triazolo[4,3-a]quinazolin-5-one, methyl 4-{7-[3-(4-methoxy-phenyl)-prop-1-ynyl]-5-oxo-5H-[1,2,4]triazolo[4,3-a]quinazolin-4-ylmethyl}-benzoate, 4-[5-oxo-7-(3-phenyl-prop-1-ynyl)-5H-[1,2,4]triazolo[4,3-a]quinazolin-4-ylmethyl]-benzoic acid, 4-(1-methyl-2,4-dioxo-6-(2-phenylethynyl)-1,4-dihydro-2H-quinazolin-3-ylmethyl)-benzoic acid, 3-(4-fluorobenzyl)-6-(3-phenyl-prop-1-ynyl)-1-methyl-1H-quinazolin-2,4-dione, 3-(4-fluorobenzyl)-6-[3-(4-methoxyphenyl)-3-oxo-prop-1-ynyl)-1-methyl-1H-quinazolin-2,4-dione, methyl 4-[1-methyl-2,4-dioxo-6-(3-phenyl-prop-1-ynyl)-1,4-dihydro-2H-quinazolin-3-ylmethyl]-benzoate, 3-(4-fluorobenzyl)-6-[3-(4-methoxyphenyl)-prop-1-ynyl]-1-methyl-1H-quinazolin-2,4-dione, 3-(3-chloro-benzyl)-1-methyl-6-(3-phenyl-prop-ynyl)-1H-quinazoline-2,4-dione,
3-(3-fluoro-benzyl)-1-methyl-6-(3-phenyl-prop-1-ynyl)-1H-quinazoline-2,4-dione,
3-(4–Chloro-benzyl)-1-methyl-6-(3-phenyl -prop-1-ynyl)-1H-quinazoline-2,4-dione,
3-(4-bromo-benzyl)-1-methyl-6-(3-phenyl-prop-1-ynyl)-1H-quinazoline-2,4-dione,
3-(3,4-difluoro-benzyl)-1-methyl-6-(3-phenyl-prop-1-ynyl)-1H-quinazoline-2,4-dione,
tert-butyl 4-[6-(3-biphenyl-4-yl-prop-1-ynyl)-1-methyl-2,4-dioxo-1,4-dihydro-2H-quinazolin-3-ylmethyl]-benzoate,
tert-butyl 4-{6-[3-(4-fluoro-phenyl)-prop-1-ynyl]-1-methyl-2,4-dioxo-1,4-dihydro-2H-quinazolin-3-ylmethyl}-benzoate,
4-[6-(3-imidazol-1-yl-prop-1-ynyl)-1-methyl-2,4-dioxo-1,4-dihydro-2H-quinazolin-3-ylmethyl]-benzoic acid-trifluoro-acetic acid,
3-(3,4-difluoro-benzyl)-6-(3-imidazol-1-yl-prop-1-ynyl)-1-methyl-1H-quinazoline-2,4-dione,
2-dimethylamino-ethyl 4-[1-methyl-2,4-dioxo-6-(3-phenyl-prop-1-ynyl)-1,4-dihydro-2H-quinazolin-3-ylmethyl]-benzoate,
4-(6-{3-[4-(tert-butyl-dimethyl-silanyloxy)-phenyl]-prop-1-ynyl}-1-methyl-2,4-dioxo-1,4-dihydro-2H-quinazolin-3-ylmethyl)-benzoic acid,
N,N-dimethyl-4-[1-methyl-2,4-dioxo-6-(3-phenyl-prop-1-ynyl)-1,4-dihydro-2H-quinazolin-3-ylmethyl]-benzamide,
1-methyl-6-(3-phenyl-prop-1-ynyl)-3-[4-(piperidine-1-carbonyl)-benzyl]-1H-quinazoline-2,4-dione,
N-ethyl-4-[1-methyl-2,4-dioxo-6-(3-phenyl-prop-1-ynyl)-1,4-dihydro-2H-quinazolin-3-ylmethyl]-benzamide,
6-[3-(4-chloro-phenyl)-prop-1-ynyl]-3-(3,4-difluoro-benzyl)-1-methyl-1H-quinazoline-2,4-dione,
3-(3-chloro-benzyl)-6-[3-(4-chloro-phenyl)-prop-1-ynyl]-1-methyl-1H-quinazoline-2,4-dione,
3-(4-hydroxymethyl-benzyl)-1-methyl-6-(3-phenyl-prop-1-ynyl)-1H-quinazoline-2,4-dione,
1-methyl-3-[4-(4-methyl-piperazine-1-carbonyl)-benzyl]-6-(3-phenyl-prop-1-ynyl)-1H-quinazoline-2,4-dione,
N,N-bis-(2-hydroxy-ethyl)-4-[1-methyl-2,4-dioxo-6-(3-phenyl-prop-1-ynyl)-1,4-dihydro-2H-quinazolin-3-ylmethyl]-benzamide,
3-(3,4-difluoro-benzyl)-6-[3-(4-fluoro-phenyl)-prop-1-ynyl]-1-methyl-1H-quinazoline-2,4-dione,
3-(3,4-difluoro-benzyl)-1-methyl-6-(3-[1,2,3]triazol-1-yl-prop-1-ynyl)-1H-quinazoline-2,4-dione,
3-(3,4-difluoro-benzyl)-1-methyl-6-(3-[1,2,4]triazol-1-yl-prop-1-ynyl)-1H-quinazoline-2,4-dione,
3-(3,4-dichloro-benzyl)-1-methyl-6-(3-[1,2,4]triazol-1-yl-prop-1-ynyl)-1H-quinazoline-2,4-dione,
and 3-(3,4-dichloro-benzyl)-1-methyl-6-(3-phenyl-prop-1-ynyl)-1H-quinazoline-2,4-dione.

The optical isomers, the N-oxides, as well as the addition salts with a pharmaceutically-acceptable acid or base, of the preferred compounds and the various embodiment of the invention form an integral part of the invention.

The invention also relates to a pharmaceutical composition comprising as active ingredient an effective amount of a compound of formula (I) together with one or more pharmaceutically-acceptable excipients or carriers.

Another embodiment of the invention concerns the use of the compound of formula (I) for the preparation of a medicinal product intended for treating a disease involving therapy by inhibition of matrix metalloprotease, and more particularly of type-13 matrix metalloprotease.

The invention also relates to a method for treating a living body afflicted with a disease involving a therapy by inhibition of matrix metalloprotease, and more particularly of type-13 matrix metalloprotease, the said method comprising the administration of an effective amount of a compound of formula (I) to a patient in need thereof.

A preferred method of treatment according to this invention is treatment of a disease selected from arthritis, rheumatoid arthritis, osteoarthritis, osteoporosis, periodontal diseases, inflammatory bowel disease, psoriasis, multiple sclerosis, cardiac insufficiency, atherosclerosis, asthma, chronic obstructive pulmonary diseases, age-related degeneration and cancers.

DETAILED DESCRIPTION OF THE INVENTION

The compounds provided by this invention are those defined in formula (I). In formula (I), it is understood that:

a ($C_1$–$C_6$)alkyl group denotes a linear or branched group containing from 1 to 6 carbon atoms; example of such groups, without implying any limitation are methyl, ethyl, propyl, isopropyl, tert-butyl, neopentyl, hexyl, a ($C_2$–$C_6$)alkenyl group denotes a linear or branched group containing from 2 to 6 carbon atoms, and one or more double bonds; examples of such groups without implying any limitation are vinyl, allyl, 3-buten-1-yl, 2-methyl-buten-1-yl, hexenyl, a ($C_2$–$C_6$)alkynyl group denotes a linear or branched group containing from 2 to 6 carbon atoms, and one or more triple bonds; examples of such groups without implying any limitation are ethynyl, propynyl, 3-butyn-1-yl, 2-methyl-butyn-1-yl, hexynyl, a ($C_1$–$C_6$)alkoxy group means the alkyl group as mentioned above bound through an oxygen atom; examples of such compounds without implying any limitation are methoxy, ethoxy, n-propyloxy, tert-butyloxy, a mono($C_1$–$C_6$)alkylamino denotes a amino group substituted by one ($C_1$–$C_6$)alkyl group as defined hereinbefore; example of such groups, without implying any limitation are methyl amino, isobutyl amino, ethylamino, a di($C_1$–$C_6$)alkylamino denotes a amino group substituted by two ($C_1$–$C_6$)alkyl groups as defined hereinbefore, each alkyl group being identical or different independently of each other; example of such groups, without implying any limitation are dimethylamino, diethylamino, an aryl group denotes an aromatic monocyclic or bicyclic system containing from 5 to 10 carbon atoms, and in the case of a bicyclic system, one of the ring of which is aromatic in character, and the other ring of which may be aromatic or partially hydrogenated; examples of such groups without implying any limitation are, phenyl, naphthyl, indenyl, benzocyclobutenyl, a heteroaryl group denotes an aryl group as described above in which 1 to 4 carbon atoms are replaced by 1 to 4 hetero atoms selected from oxygen, sulfur and nitrogen examples of such groups without implying any limitation are furyl, thienyl, pyrrolyl, pyrazolyl, pyridyl, pyrimidyl, pyrazinyl, benzofuryl, benzothienyl, indolyl, quinolyl, isoquinolyl, imidazolyl, benzodioxolyl, benzodioxinyl, benzo[1,2,5]thiadiazolyl, benzo[1,2,5]oxadiazolyl, [1,2,3]triazolyl, [1,2,4]triazolyl, a cycloalkyl group denotes a monocyclic or bicyclic system containing from 3 to 10 carbon atoms, this system being saturated or partially unsaturated but without aromatic character; examples of such groups without implying any limitation are cyclopropyl, cyclobutyl, cyclopentyl, cyclohexyl, cyclooctyl, cycloheptyl, adamantyl, decalinyl, norbornyl, a heterocycloalkyl group denotes a cycloalkyl group as defined hereinbefore in which 1 to 4 carbon atoms are replaced by 1 to 4 hetero atoms selected from oxygen, sulfur, and nitrogen, a bicycle denotes two fused-monocycle or two bridged-monocycle, a trihalogeno($C_1$–$C_6$)alkyl group denotes an alkyl group as defined above which contains a trihalogeno group; examples of such groups without implying any limitation are trifluoromethyl, 2,2,2-trifluoroethyl, a ($C_1$–$C_7$)acyl group denotes an alkyl group or a phenyl group as defined above bound through a carbonyl group; examples of such groups without implying any limitation are acetyl, ethylcarbonyl, benzoyl, a multiple bond denotes double bond or triple bond, a halogen atom means fluoro, chloro, bromo or iodo, optical isomers refer to racemates, enantiomers and diastereoisomers.

The invention also relates to the pharmaceutically acceptable salts of the compounds of formula (I). A review of the pharmaceutically acceptable salts will be found in *J. Pharm. Sci.*, 1977, 66, 1–19.

Pharmaceutically acceptable acids mean non-toxic mineral or organic acids. Among those there may be mentioned, without implying any limitation, hydrochloric acid, hydrobromic acid, sulfuric acid, phosphonic acid, nitric acid, citric acid, acetic acid, trifluoroacetic acid, lactic acid, pyruvic acid, malonic acid, succinic acid, glutaric acid, fumaric acid, tartaric acid, maleic acid, ascorbic acid, oxalic acid, methanesulfonic acid, camphoric acid, benzoic acid, toluenesulfonic acid, etc. . . .

Pharmaceutically acceptable bases mean non-toxic mineral or organic bases. Among those, there may be mentioned, without implying any limitation, sodium hydroxide, potassium hydroxide, calcium hydroxide, triethylamine, tert-butylamine, dibenzylethylenediamine, piperidine, pyrrolidine, benzylamine, quaternary ammonium hydroxides etc. . . .

The invention also relates to a process for the preparation of compounds of formula (I), which uses as starting material a compound of formula (II):

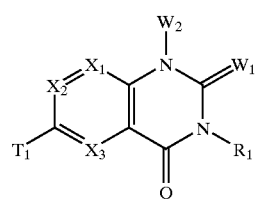

(II)

in which $R_1$, $W_1$, $W_2$, $X_1$, $X_2$ and $X_3$ have the same definitions as the compounds of formula (I), and $T_1$ represents a group selected from hydrogen, halogen, mesylate, triflate, formyl, acetyl, and ester, compound of formula (II) which is treated:

either when $T_1$ represents an halogen atom, a mesylate group, or a triflate group, in the presence of a base under conditions of palladium-catalyzed alkynylation with a compound of formula (III):

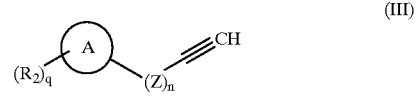

(III)

in which A, Z, $R_2$, q and n are as defined for the compounds of formula (I), to yield the compounds of formula (I),

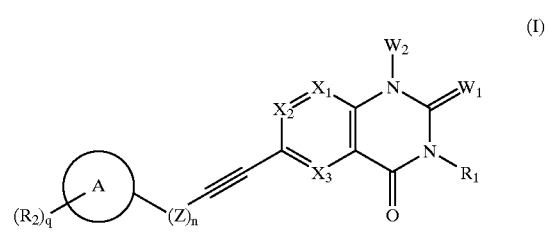

(I)

or when $T_1$ represents an hydrogen atom, with iodine to yield in situ the corresponding iodide intermediate, which is treated directly without isolation or purification, with a compound of formula (III) as described hereinbefore, under conditions of palladium-catalyzed alkynylation in the presence of a base, to yield the compounds of formula (I), or when $T_1$ represents an iodine atom, with 2-trimethylsilylacetylene under conditions of palladium-catalyzed alkynylation in the presence of a base, to yield the compounds of formula (IVa):

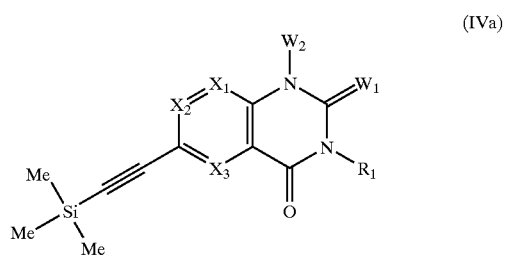

(IVa)

in which $R_1$, $W_1$, $W_2$, $X_1$, $X_2$ and $X_3$ are as defined hereinbefore, and subsequently treated the compound of formula (IVa) with a strong base in polar solvant, to yield the free alcyne compound of formula (IV):

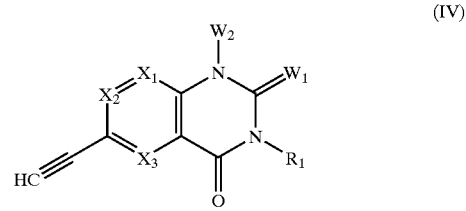

(IV)

in which $R_1$, $W_1$, $W_2$, $X_1$, $X_2$ and $X_3$ are as defined hereinbefore, or when $T_1$ represents an acetyl group, first with lithium diisopropylamine at −78° C. in an inert solvent to provide an enolate, second with diethyl chlorophosphate and subsequently with lithium diisopropylamine, to yield a compound of formula (IV):

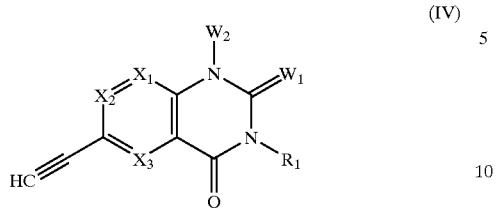

in which $R_1$, $W_1$, $W_2$, $X_1$, $X_2$ and $X_3$ are as defined hereinbefore, and condensing the compound of formula (IV), in the presence of triphenylphosphin and $PdCl_2(PPh_3)_2$, under basic conditions to a compound of formula (V):

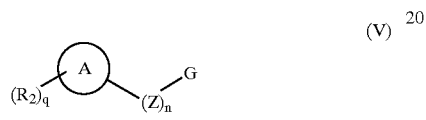

in which A, Z, $R_2$, q and n are as defined hereinbefore and G represents a leaving group, to yield the compound of formula (I),

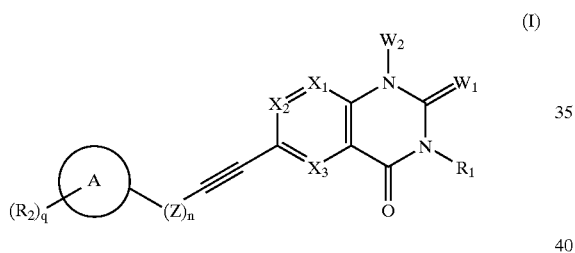

or when $T_1$ represents an ester group, with a reductive agent, to yield the corresponding aldehyde compound of formula (VI):

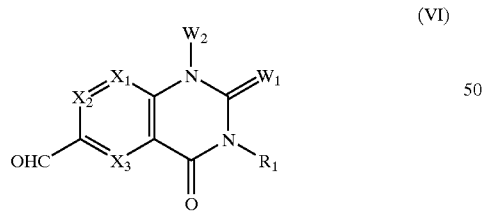

in which $R_1$, $W_1$, $W_2$, $X_1$, $X_2$ and $X_3$ are as defined hereinbefore, and subsequently:

either condensing said compound of formula (VI), in basic conditions, with diazomethyl trimethyl silane or with diazomethyl diethoxy phosphonate, to yield, after basic treatment, a compound of formula (IV) as defined hereinbefore:

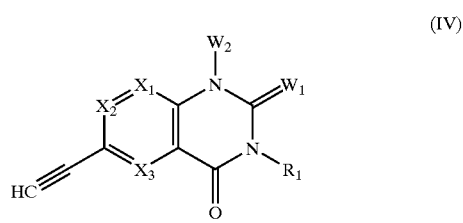

and adding said compound of formula (IV) to a compound of formula (V) as described hereinbefore:

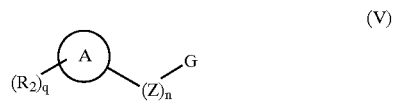

in which $R_2$, A, Z, q, n and G are as defined hereinbefore, to yield the compound of formula (I), or reacting, said compound of formula (VI), with tetrabromomethane in the presence of triphenylphosphine in an aprotic solvent to yield a compound of formula (VII):

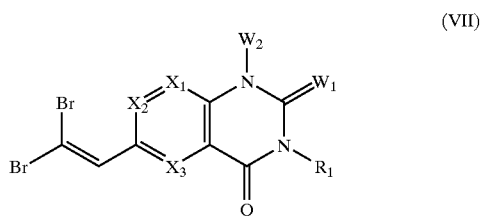

in which $R_1$, $W_1$, $W_2$, $X_1$, $X_2$ and $X_3$ are as defined hereinbefore, and dehalogenating said compound of formula (VII) through treatment with a strong base in an inert solvent, or with butyllithium in presence of triphenylphosphine and zinc, to yield the compound of formula (IV) as defined hereinbefore, and reacting said compound of formula (IV) with a compound of formula (V) as defined in the previous step to yield a compound of a general formula (I):

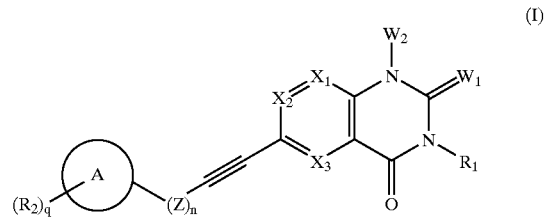

The compounds of formula (I) are purified, where appropriate, according to a conventional purification technique, and separated, where appropriate, into their different isomers according to a conventional separation technique, and converted, where appropriate, into addition salts thereof with a pharmaceutically-acceptable acid or base.

The compounds of formula (IV):

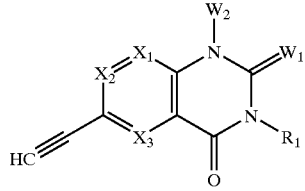

(IV)

wherein $W_1$, $W_2$, $X_1$, $X_2$, $X_3$ and $R_1$ are as defined in compounds of formula (I) are novel useful intermediates for the preparation of compounds of formula (I).

The compounds of formula (VI)

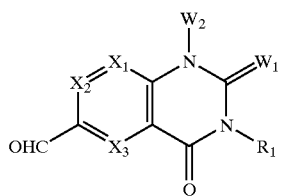

(VI)

wherein $W_1$, $W_2$, $X_1$, $X_2$, $X_3$ and $R_1$ are as defined in compounds of formula (I) are also novel useful intermediates for the preparation of compounds of formula (I).

The compounds of formula (II) used as starting material may be distinguished into two groups which are respectively represented:

by the compounds of the formula (II/A):

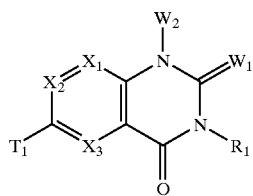

(II/A)

wherein:
$W_1$ represents an oxygen atom, a sulfur atom, or a —$NR_3$ group in which $R_3$ represents hydrogen atom, ($C_1$–$C_6$) alkyl, hydroxyl or cyano,
$W_2$ represents a group selected from:
hydrogen atom, trifluoromethyl, amino, mono($C_1$–$C_6$) alkylamino, di($C_1$–$C_6$)alkylamino,
($C_1$–$C_6$)alkyl, ($C_2$–$C_6$)alkenyl, ($C_2$–$C_6$)alkynyl, aryl, aryl ($C_1$–$C_6$)alkyl, cycloalkyl($C_1$–$C_6$)alkyl, 5- or 6-membered monocycle heteroaryl, and 5- or 6-membered monocycle heterocycloalkyl, each of these groups being optionally substituted by one to four groups, which may be identical or different independently of each other, selected from halogen, amino, mono($C_1$–$C_6$)alkylamino, di($C_1$–$C_6$)alkylamino, cyano, trihalogeno($C_1$–$C_6$)alkyl, ($C_1$–$C_7$)acyl, —C(=O)$OR_4$, —$OR_4$ and —$SR_4$, wherein $R_4$ represents a hydrogen atom or a ($C_1$–$C_6$)alkyl group,
$T_1$ represents a group selected from hydrogen, halogen, mesylate, triflate, formyl, acetyl, and ester, and $R_1$, $X_1$, $X_2$, and $X_3$ are as defined in the compounds of formula (I), and by the compounds of formula (II/B):

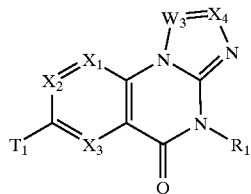

(II/B)

wherein:
$W_3$ represents a nitrogen atom or a group —$CR_5$ in which $R_5$ is selected from:
a hydrogen atom,
—$OR_6$, —$SR_6$ in which $R_6$ is selected from hydrogen, ($C_1$–$C_6$)alkyl and aryl($C_1$–$C_6$)alkyl;
($C_1$–$C_6$)alkyl, cycloalkyl, aryl, aryl($C_1$–$C_6$)alkyl, heteroaryl, and heterocycloalkyl, each of these groups being optionally substituted by a group selected from —($CH_2$)$_p$—OH and —($CH_2$)$_p$—$NH_2$, wherein p is an integer from 0 to 4 inclusive,
$X_4$ represents a nitrogen atom or a group —$CR_7$ in which $R_7$ is selected from hydrogen, —$NR_8R_9$, —$OR_8$, —$SR_8$, ($C_1$–$C_6$)alkyl, cycloalkyl, aryl, aryl($C_1$–$C_{10}$)alkyl, heteroaryl, and heterocycloalkyl,
each of these groups being optionally substituted by a group selected from —($CH_2$)$_p$—OH and —($CH_2$)$_p$—$NH_2$, wherein p is as defined hereinbefore,
and in which $R_8$ and $R_9$, identical or different independently of each other, are selected from hydrogen, ($C_1$–$C_6$)alkyl and aryl($C_1$–$C_6$)alkyl,
$T_1$ represents a group selected from hydrogen, halogen, mesylate, triflate, formyl, acetyl, and ester, and $R_1$, $X_1$, $X_2$, and $X_3$ are as defined in the compound of formula (I).

In an advantageous embodiment of the invention, the process for the preparation of compounds of formula (I) comprises the following step:
reacting as starting material, a compound of formula (II/A):

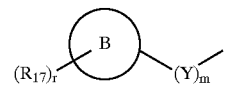

(II/A)

in which $W_1$ represents an oxygen atom, $W_2$ represents a ($C_1$–$C_6$)alkyl group, $X_1$ represents a —CH group, $X_2$ represents a nitrogen atom or a —CH group, $X_3$ represents a —CH group, and $T_1$ represent a iodine atom or a triflate group, and $R_1$ represents a group of formula:

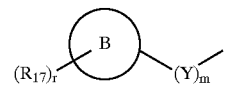

in which Y represents a methylene group, m is equal to one, B represents a phenyl group, $R_{17}$ is as defined in the compound of formula (I) and r is equal to one, with, as reagent, a compound of formula (III):

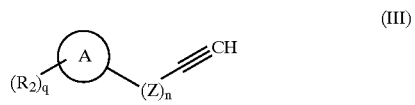

in which Z represents a methylene group, n is equal to one, A is a phenyl group, q is equal to zero or one, and $R_2$ is as defined in the compound of formula (I), to yield a compound of formula (I/a), which constitutes a particular subgroup of the compounds of formula (I):

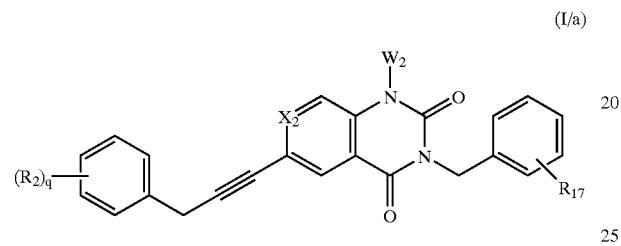

in which $W_2$, $X_2$, $R_2$, q and $R_{17}$ are as defined hereinbefore.

The compounds of formula (II/A)

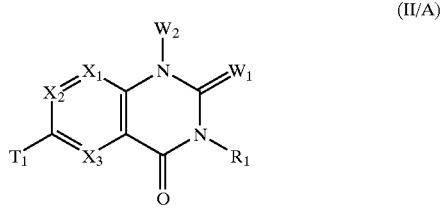

wherein:

$W_1$ represents an oxygen atom, a sulfur atom, or a —$NR_3$ group in which $R_3$ represents hydrogen atom, ($C_1$–$C_6$) alkyl, hydroxyl or cyano, $W_2$ represents a group selected from:
hydrogen atom, trifluoromethyl, amino, mono($C_1$–$C_6$) alkylamino, di($C_1$–$C_6$)alkylamino,
($C_1$–$C_6$)alkyl, ($C_2$–$C_6$)alkenyl, ($C_2$–$C_6$)alkynyl, aryl, aryl ($C_1$–$C_6$)alkyl, cycloalkyl($C_1$–$C_6$)alkyl, 5- or 6-membered monocycle heteroaryl, and 5- or 6-membered monocycle heterocycloalkyl, each of these groups being optionally substituted by one to four groups, which may be identical or different independently of each other, selected from halogen, amino, mono($C_1$–$C_6$)alkylamino, di($C_1$–$C_6$)alkylamino, cyano, trihalogeno($C_1$–$C_6$)alkyl, ($C_1$–$C_7$)acyl, —C(=O)O$R_4$, —O$R_4$ and —S$R_4$, wherein $R_4$ represents a hydrogen atom or a ($C_1$–$C_6$)alkyl group, $T_1$ represents a halogen atom, and $R_1$, $X_1$, $X_2$, and $X_3$ are as defined in the compounds of formula (I), are also novel useful intermediates for the preparation of compounds of formula (I).

The compounds of formula (II/A) may be obtained through the synthetic way described in scheme 1.

Scheme 1

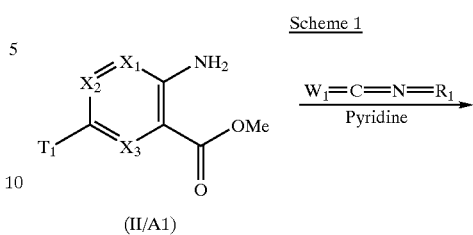

(II/A1)

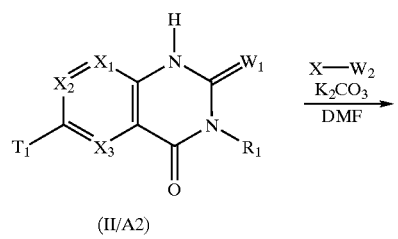

(II/A2)

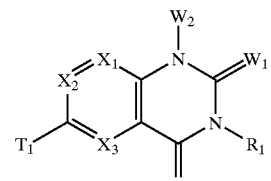

(II/A)

In these compounds of formulae (II/A1) and (II/A2), the substituents $X_1$, $X_2$, $X_3$, $W_1$, $W_2$, $R_1$ and $T_1$ are as defined in the compounds of formula (II/A). In the compound X-$W_2$, $W_2$ is as defined hereinbefore and X represents a leaving group.

The starting material (II/A1) is either a commercial product or is obtained according to conventional methods of organic synthesis well known to the person skilled in the art.

In another preferred embodiment, compounds of formula (II/A), where $W_1$ represents an oxygen atom or a sulfur atom, may be obtained through the synthetic way described in scheme 2.

Scheme 2

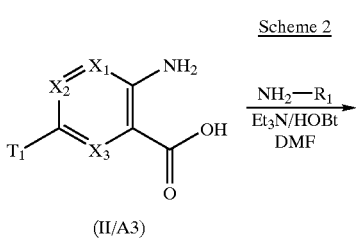

(II/A3)

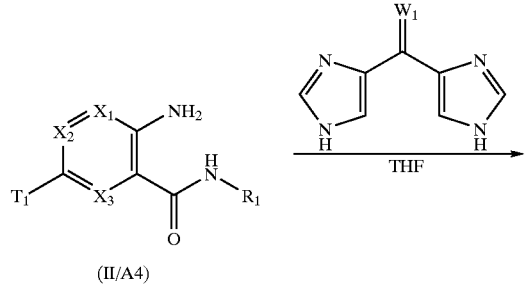

(II/A4)

-continued

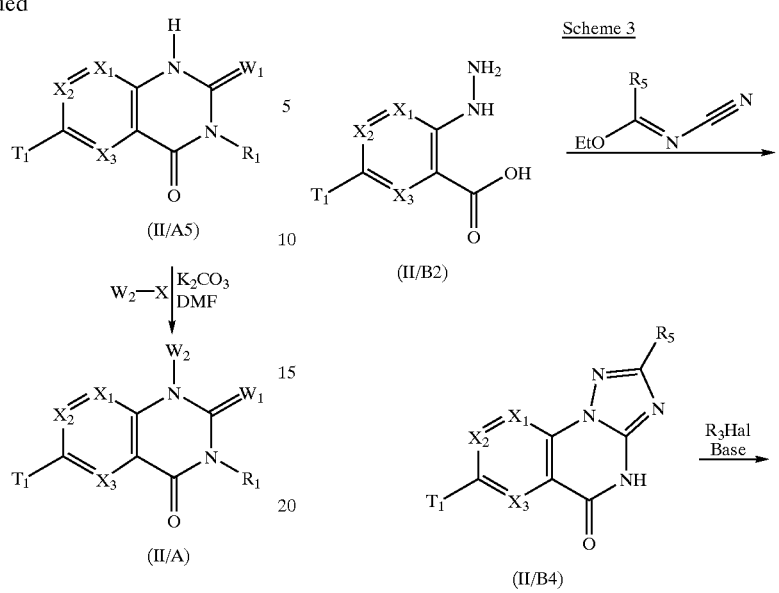

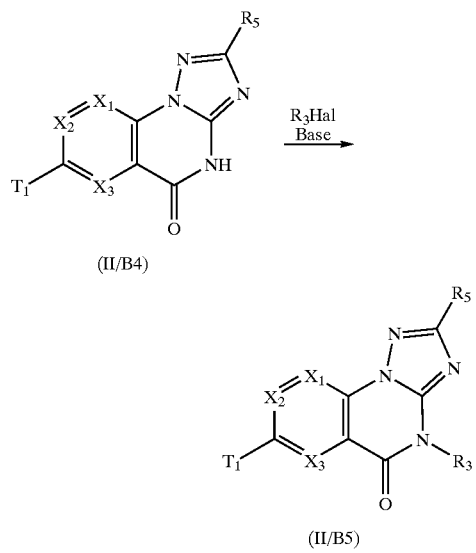

In a first step the acid function of compound (II/A3) is transformed into an amide group by reaction with a primary amine in usual conditions of organic chemistry to yield the compound (II/A4). This intermediate is then treated with 1,1'-carbonyldiimidazole or 1,1'-thiocarbonyldiimidazole, depending whether $W_1$ is an oxygen atom or a sulfur atom, in anhydrous tetrahydrofuran, to yield a compound of formula (II/A5), which is treated in the same conditions as those described in scheme 1 to obtain the compound of formula (II/A).

Compounds of the formula (II/B) are obtained through the synthetic way described in scheme 3 and in scheme 4.

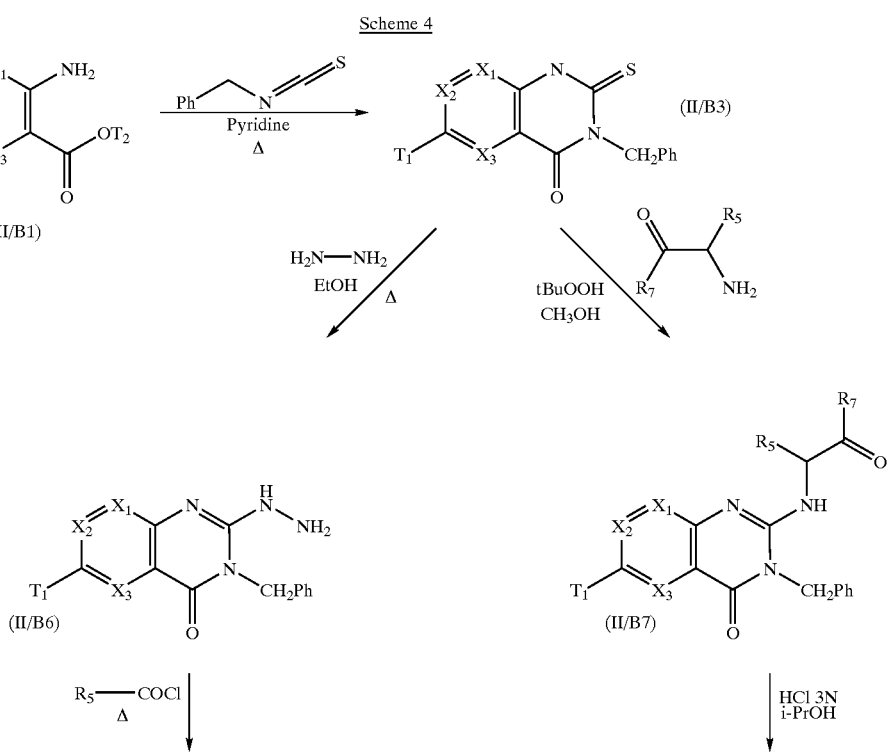

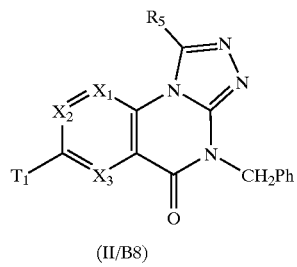

(II/B8)

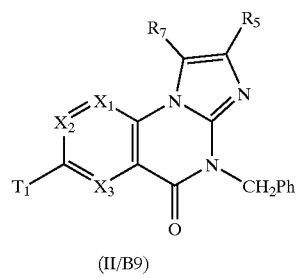

(II/B9)

1) AlCl₃
2) R₃Hal/base

1) AlCl₃
2) R₃Hal base

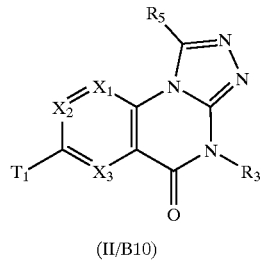

(II/B10)

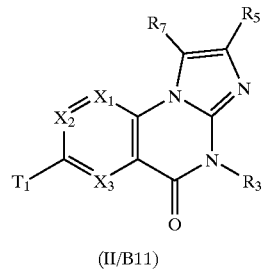

(II/B11)

In Scheme 3 the compound (II/B5) is obtained from substrate (II/B2) which is commercially available or obtained through usual methods of organic synthesis. The compound (II/B2) is treated with an alkyl N-cyanoimidate to give a compound of formula (II/B4). The substitution of NH in position 4 with a halide in the presence of a base like cesium carbonate in an aprotic solvent leads to the formation of a compound of formula (II/B5) which represents a particular subgroup of compounds of formula (II) used as starting material in the general process for manufacturing compounds of formula (I).

In Scheme 4 the compound (II/B10) is obtained starting from compound (II/B1) which is treated in a first step with benzyl isothiocyanate to give the thiocarbonyl derivative (II/B3). This compound is heated, in a refluxing alcohol, in the presence of hydrazine hydrate to give the corresponding hydrazine (II/B6) which is in turn cyclized by reaction with an acid chloride or an orthoester to yield compound of formula (II(B8). This compound is then debenzylated by usual treatment and the N4-debenzylated atom is substituted by a halide in a basic medium, for example by addition of cesium carbonate in dimethylformamide to yield the product of formula (II/B10). The compound of formula (II/B10) is a particular subgroup of the compounds of formula (II) used as starting material in the general process for manufacturing compounds of formula (I).

In Scheme 4, the compound (II/B11) is obtained starting from compound (II/B1) which is transformed in a first step into a compound of formula (II/B3) as described hereinbefore. This compound (II/B3) is then treated in an alcoholic solvent such as methanol or ethanol, in the presence of a peroxide for initiating the oxidation of the starting thiol. The amino ketone (II/B6) obtained thereby is readily cyclized in the presence of acid, in an alcoholic solvent such as isopropanol to yield a compound of formula (II/B9) which is debenzylated and subsequently substituted on the N4 as described hereinbefore in order to obtain the product of formula (II/B11). The compound of formula (II/B11) is a particular subgroup of the compounds of formula (II) used as starting material in the general process for manufacturing compounds of formula (I).

Generally, isomers of the compounds of the invention are understood to be optical isomers such as enantiomers and diastercoisomers. More especially, pure enantiomeric forms of the compounds of the invention may be separated by starting from mixtures of enantiomers which are reacted with a racemate-separating agent that can be released, the said agent being itself in the form of a pure enantiomer, which allows the corresponding diastereoisomers to be obtained. The diastereoisomers are then separated according to the separation techniques well known to the person skilled in the art, such as crystallization or chromatography, and the separating agent is then removed using conventional techniques of organic synthesis, resulting in a pure enantiomer.

The compounds of the invention that are present in the form of a mixture of diastereoisomers are isolated in a pure form by using conventional separation techniques such as chromatography.

As mentioned above, compounds of formula (I) of the present invention are matrix metalloprotease inhibitors, and more particularly inhibitors of the enzyme MMP-13.

In this respect, their use is recommended for the treatment of diseases or complaints involving a therapy by MMP-13 inhibition. By way of example, the use of the compounds of the present invention may be recommended for the treatment of any pathology in which destruction of extracellular matrix tissue occurs, and most particularly pathologies such as arthritis, rheumatoid arthritis, osteoarthritis, osteoporosis, periodontal diseases, inflammatory bowel disease, psoriasis, multiple sclerosis, cardiac insufficiency, atherosclerosis, asthma, chronic obstructive pulmonary disease, age-related macular degeneration and cancers.

The present invention also relates to pharmaceutical compositions comprising as active ingredient at least one compound of formula (I), an isomer thereof, a N-oxide thereof, or an addition salt thereof with a pharmaceutically-acceptable acid or base, alone or in combination with one or more pharmaceutically-acceptable, inert, non-toxic excipients or carriers.

Among the pharmaceutical compositions according to the invention, there may be mentioned more especially those that are suitable for oral, parenteral (intravenous, intramuscular or subcutaneous), per- or trans-cutaneous, intravaginal, rectal, nasal, perlingual, buccal, ocular or respiratory administration.

Pharmaceutical compositions according to the invention for parenteral injections especially include aqueous and non-aqueous sterile solutions, dispersions, suspension and emulsions, and also sterile powders for reconstituting injectable solutions or dispersions.

Pharmaceutical compositions according to the invention for oral administration in solid form especially include tablets or dragées, sublingual tablets, sachets, gelatin capsules and granules, for oral, nasal, buccal or ocular administration in liquid form, especially include emulsions, solutions, suspensions, drop, syrups and aerosols.

Pharmaceutical compositions for rectal or vaginal administration are preferably suppositories, and those for per- or trans-cutaneous administration especially include powders, aerosols, creams, ointment, gels and patches.

The pharmaceutical compositions mentioned hereinbefore illustrate the invention but do not limit it in any way.

Among the pharmaceutically acceptable, inert, non-toxic excipients or carriers there may be mentioned, by way of non-limiting example, diluents, solvents, preservatives, wetting agents, emulsifiers, dispersing agents, binders, swelling agents, disintegrating agents, retardants, lubricants, absorbents, suspending agents, colorants, aromatizing agents etc. . . .

The useful dosage varies according to the age and weight of the patient, the administration route, the pharmaceutical composition used, the nature and severity of the disorder and the administration of any associated treatments. The dosage ranges from 2 mg to 1 g per day in one or more administrations. The compositions are prepared by methods that are common to those skilled in the art and generally comprise 0.5% to 60% by weight of active principle (compound of formula (I)) and 40% to 99.5% by weight of pharmaceutically acceptable excipients or carriers.

The examples that follow illustrate the invention but do not limit it in any way.

The starting materials used are products that are known or that are prepared according to known operating procedures. The various preparations yield synthetic intermediates that are useful in preparation of the compounds of the invention. Some of these intermediates are new compounds.

The structures of the compounds described in the Examples and Preparations were determined according to the usual spectrophotometric techniques (infrared, nuclear magnetic resonance, mass spectrometry, . . . )

In the Preparations and Examples, it is understood that:
DMF means Dimethylformamide,
THF means Tetrahydrofurane,
DMSO means Dimethylsulfoxyde,
TOTU means O-(ethoxycarbonyl)cyanomethylamino]-N—N—N'-N'-tetramethyl uronium fluoroborate,
EDAC means 1-(3-dimethylaminopropyl)-3-ethylcarbodiimide hydrochloride,
and HOBT means 1-hydroxybenzotriazole hydrate.

EXAMPLES

Preparation A: 4-(6-Iodo-1-methyl-2,4-dioxo-1,4-dihydro-2H-quinazolin-3-ylmethyl)-benzoic acid Step 1: Methyl 4-[(2-amino-5-iodo-benzoylamino)-methyl]-benzoate To a stirred solution of 15 g (74.4 mmol) of methyl 4-(aminomethyl)benzoate hydrochloride, 300 ml of dimethylformamide and 10.3 ml (7.53 g, 74.4 mmol) of triethylamine were added, at room temperature, followed by 10.06 g (74.4 mmol) of 1-hydroxybenzotriazole hydrate, 19.6 g (74.4 mmol) of 2-amino-5-iodobenzoic acid and 14.3 g (74.4 mmol) of 1-(3-dimethylaminopropyl)-3-ethyl carbodiimide hydrochloride. After stirring at room temperature overnight, the mixture was concentrated and the residue was dissolved in 300 ml of dichloromethane. The organic phase was washed with 150 ml $H_2O$, 150 ml HCl 1N, and 150 ml $H_2O$, dried over sodium sulfate and concentrated. The residue was recrystallized from 170 ml acetonitrile to afford after filtration 19.6 g of the desired product (yield: 70%).

N.M.R: DMSO $^1$H δ (ppm): 3.8 (s, 3H); 4.45 (d, 2H); 6.5–6.6 (m, 3H); 7.3–7.45 (m, 3H); 7.8–7.95 (m, 3H); 8.9 (t, 1H).

Purity (HPLC): 99.1%

Step 2: Methyl 4-(6-iodo-2,4-dioxo-1,4-dihydro-2H-quinazolin-3-ylmethyl)-benzoate To a solution of 21.35 g (52 mmol) of the compound obtained in Step 1 in 400 ml of dry tetrahydrofurane were added 9.3 g (57.2 mmol) of 1,1'-carbonyldiimidazole. The solution was heated overnight to 60° C. After cooling the precipitate was filtered and dried to afford 19.6 g of the desired product (yield: 68.3%).

N.M.R: DMSO $^1$H δ (ppm): 3.8 (s, 3H); 5.1 (s, 2H); 6.95–7.05 (m, 1H); 7.35–7.45 (m, 2H); 7.8–7.90 (m, 2H); 7.9–8.0 (m, 1H); 8.2 (s, 1H); 11.6 (bs, 1H).

Purity (HPLC): 99.5%

Step 3: Methyl 4-(6-iodo-1-methyl-2,4-dioxo-1,4-dihydro-2H-quinazolin-3-ylmethyl)-benzoate To a stirred suspension of 11 g (25.2 mmol) of the compound obtained in Step 2 and 110 ml of dry DMF were added 5.22 g (37.8 mmol) of $K_2CO_3$, at room temperature. After 15 minutes, 7.85 ml (17.9 g, 126 mmol) of iodomethane were added. The reaction mixture was stirred for 2 hours and the precipitate filtered off and dissolved in a mixture of dichloromethane/methanol. The organic phase was washed with $H_2O$, dried over $Na_2SO_4$ and concentrated to afford a precipitate corresponding to the desired product (10.1 g; yield: 89%).

N.M.R: DMSO $^1$H δ (ppm): 3.5 (s, 3H); 3.8 (s, 3H); 5.2 (s, 2H); 7.30 (d, 1H); 7.45 (d, 2H); 7.90 (d, 2H); 8.1 (d, 1H); 8.3 (s, 1H).

Purity (HPLC): 96.7%

Step 4: 4-(6-Iodo-1-methyl-2,4-dioxo-1,4-dihydro-2H-quinazolin-3-ylmethyl)-benzoic acid A mixture of 3.0 g (6.66 mmol) of the compound obtained in Step 3, 30 ml of dioxane, 120 ml $H_2O$, and 0.56 g (13.3 mmol) of $LiOH,H_2O$ was heated to reflux over 1 hour. After cooling and acidification with concentrated hydrochloric acid, the precipitate obtained was filtered off and recrystallized in dioxane/ether to afford 1.85 g of the desired product (yield: 64.2%).

N.M.R: DMSO $^1$H δ (ppm): 3.5 (s, 3H); 5.2 (s, 2H); 7.30 (d, 1H); 7.40 (d, 2H); 7.85 (d, 2H); 8.1 (d, 1H); 8.30 (s, 1H); 12.9 (bs, 1H)

Purity (HPLC): 98.0%

Preparation B: 4-(1-Methyl-2,4-dioxo-6-trifluoromethanesulfonyloxy-1,4-dihydro-2H-pyrido[3,4-d]pyrimidin-3-ylmethyl)-benzoic acid Step 1: 5-(tert-Butoxycarbonylamino)-2-methoxypyridine-4-carboxylic acid The compound 5-(tert-butoxycarbonylamino)-2-methoxypyridine-4-carboxylic acid was prepared using the procedure described in *J. Chem. Soc., Perkin Trans I*, 1996, 18, 2221–2226.

Step 2: Methyl 4-{[(5-tert-butoxycarbonylamino-2-methoxy-pyridine-4-carbonyl)-amino]-methyl}-benzoate 9 g (33.5 mmol) of the compound obtained in Step 1, 320 ml of dichloromethane, 11 g (33.5 moles) of TOTU and 6.1 g (36.9 mmol) of methyl-(4-aminomethyl)benzoate were stirred and cooled to 0° C., and then 11.6 ml (8.6 g, 67 mmol) of diisopropylamine added. The mixture was stirred for 15 minutes at 0° C. and then overnight at room temperature. The reaction mixture was washed successively with 200 ml $NH_4OH$, 200 ml $H_2O$, 200 ml HCl 10%, 200 ml $H_2O$, 200 ml $NaHCO_3$, and 200 ml $H_2O$. The organic phase was dried over $Na_2SO_4$, filtered, and concentrated under vacuum. The residue was crystallized in a mixture of dichloromethane/ether to afford 10.5 g of the desired product (yield: 73.3%).

TLC: $CH_2Cl_2$/MeOH: 95/5 v/v Rf=0.60
N.M.R: $CDCl_3$ $^1H$ δ (ppm): 1.50 (s, 9H); 3.90 (2s, 6H); 4.60 (d, 2H); 6.70 (s, 1H); 7.0 (bs, 1H); 7.4 (d, 2H); 8.0 (d, 2H); 8.75 (bs, 1H); 8.9 (s, 1H).

Step 3: Methyl 4-{[(5-amino-2-methoxy-pyridine-4-carbonyl)-aminomethyl}-benzoate To a solution of 4.8 g (11.5 mmol) of the compound obtained in Step 2 in 100 ml of dichloromethane were added 20 ml of trifluoroacetic acid. The reaction was heated to 40° C. for 1 hour, and then concentrated under vacuum. The residue was taken up in a mixture of dichloromethane and $H_2O$ then basified with NaOH. After separation by decantation, the organic phase was washed, dried over $Na_2SO_4$, and concentrated under vacuum to afford 3.5 g of a yellow precipitate corresponding to the desired product (yield: 97%).

TLC: $CH_2Cl_2$/MeOH 95/5 v/v Rf=0.40
N.M.R: $CDCl_3$ $^1H$ δ (ppm): 3.8 (s, 3H); 3.9 (s, 3H); 4.6 (d, 2H); 4.7 (s, 2H); 6.7 (s, 1H); 6.75–6.85 (m, 1H); 7.40 (d, 2H); 7.75 (s, 2H); 8.0 (d, 2H).

Step 4: Methyl 4-(6-methoxy-2,4-dioxo-1,4-dihydro-2H-pyrido[3,4d]-pyrimidin-3-ylmethyl)-benzoate To a solution of 2.5 g (7.9 mmol) of the compound obtained in Step 3 in 110 ml of dry THF were added 2 g (12.4 mmol) of 1,1'-carbonyldiimidazole. The reaction mixture was heated to 60° C. for 24 hours. After cooling, 50 ml $H_2O$ were added and the mixture was stirred for 30 minutes to 0° C. The precipitate was filtered and washed successively with $H_2O$, MeOH and dichloromethane to afford 2.38 g of the desired product (yield: 88.3%).

TLC: $CH_2Cl_2$/MeOH 95/5 v/v Rf=0.45
N.M.R: DMSO $^1H$ δ (ppm): 3.80 (s, 3H); 3.90 (s, 3H); 5.10 (s, 2H); 7.2 (s, 1H); 7.45 (d, 2H); 7.90 (d, 2H); 8.25 (s, 1H); 11.6 (s, 1H).

Step 5: Methyl 4-(6-methoxy-1-methyl-2,4-dioxo-1,4-dihydro-2H-pyrido[3,4-d]pyrimidin-3-ylmethyl)-benzoate 2.38 g (7 mmol) of the compound obtained in Step 4 and 52 ml of dry DMF were stirred and heated until dissolution. After cooling to 25° C., 1.45 g (10 mmol) of $K_2CO_3$ and 2.2 ml (5.7 g, 35 mmol) of iodomethane were added. The mixture was stirred for 30 minutes at room temperature, then concentrated under vacuum. The residue was treated with $H_2O$ and the precipitate filtered off, washed with methanol, then dissolved in dichloromethane. The organic phase was washed with $H_2O$, dried over $Na_2SO_4$ and concentrated under vacuum. The product was crystallised in ether and filtered to afford 2.0 g of the desired product (yield: 80%).

TLC: $CH_2Cl_2$/MeOH 95/5 v/v Rf=0.95
Purity (HPLC): 98.5%
N.M.R: DMSO $^1H$ δ (ppm): 3.50 (s, 3H); 3.80 (s, 3H); 3.90 (s, 3H); 5.20 (s, 2H); 7.3 (s, 1H); 7.45 (d, 2H); 7.90 (d, 2H); 8.50 (s, 1H).

Step 6: 4-(6-Hydroxy-1-methyl-2,4-dioxo-1,4-dihydro-2H-pyrido[3,4-d]pyrimidin-3-ylmethyl)-benzoic acid 1.4 g (3.93 mmol) of compound obtained in Step 5, and 14 ml of hydrobromic acid were heated to reflux for 1 hour. After cooling, 30 ml of $H_2O$ were added and the precipitate was filtered off and washed with $H_2O$ and MeOH to afford 1.1 g of the desired product (yield: 85.5%)

TLC : $CH_2Cl_2$/MeOH 90/10 v/v Rf=0.10
N.M.R : DMSO $^1H$ δ (ppm) 3.50 (s, 3H); 5.20 (s, 2H); 7.05 (s, 1H); 7.40 (d, 2H); 7.90 (d, 2H); 8.20 (s, 1H); 10.4–13.0 (bs, 2H).

Step 7: 4-(1-Methyl-2,4-dioxo-6-trifluoromethanesulfonyloxy-1,4-dihydro-2H-pyrido[3,4-d]pyrimidin-3-ylmethyl)-benzoic acid A solution of 1.2 g of compound obtained in Step 6 in 14 ml of dry pyridin was stirred and cooled to 0° C., and then 1.5 ml (2.52 g, 9 mmol) of trifluoromethanesulfonic anhydride were added. The reaction was allowed to stir at 0° C. for 30 minutes then quenched with 30 ml of $H_2O$ and dichloromethane. The organic phase was washed with $H_2O$, HCl 10%, and $H_2O$. After concentration the residue was crystallised in a mixture dichloromethane/ether to afford 0.5 g of the desired product (yield: 30%).

TLC: $CH_2Cl_2$/MeOH 90/10 v/v Rf=0.55
N.M.R: DMSO $^1H$ δ (ppm): 3.55 (s, 3H); 5.20 (s, 2H); 7.45 (d, 2H); 7.90 (d, 2H); 8.10 (s, 1H); 8.80 (s, 1H); 12.9 (bs, 1H).

Preparation C: Methyl 4-(5-oxo-7-(Trifluoromethylsulfonyloxy)-5H-[1,2,4]triazolo[4,3-a]quinazolin-4-ylmethyl)-benzoate Step 1: 4-Benzyl-7-(trifluoromethylsulfonyloxy)-4H-[1,2,4]triazolo[4,3a]quinazolin-5-one To a suspension of 41.3 g (141.3 mmol) of 4-benzyl-7-hydroxy-4H-[1,2,4]triazolo[4,3-a]quinazolin-5-one (obtained as described in WO 00/66584) in 500 ml of $CH_2Cl_2$, 25 g (148.3 mmol) of trifluoromethylsulfonylchloride were added under stirring. Then, 22.5 g (222.5 mmol) of triethylamine were added dropwise while maintaining the internal temperature between 15 and 20° C. After the completion of addition, stirring was continued at room temperature for 4 hours. After removal of the insoluble solid by filtration, the organic solution was washed with water and brine, then dried over $Na_2SO_4$ and concentrated, providing 33.1 g of crude solid, which was purified by chromatography (cyclohexane/AcOEt: 25/75 v/v) to afford 22.5 g of the desired compound (yield: 37.5%).

TLC : $CH_2Cl_2$/MeOH 95/5 v/v Rf=0.45

Step 2: 7-(Trifluoromethylsulfonyloxy)-4H-[1,2,4]triazolo[4,3-a]quinazolin-5-one A suspension of 10.0 g (23.5 mmol) of the compound obtained in Step 1 and 18.8 g (141 mmol) of aluminium chloride in 200 ml anhydrous benzene was heated at 50° C., under stirring, for 1 h 30. After cooling, the mixture obtained was poured on water/ice. After stirring and homogenization, the insoluble solid was isolated by filtration, washed with several portions of water until neutral pH and dried, then finally washed with a portion of $CH_2Cl_2$, leaving 7.95 g (99%) of the desired compound.

TLC: $CH_2Cl_2$/MeOH 95/5 v/v Rf=0.10

Step 3: Methyl 4-(5-oxo-7-(Trifluoromethylsulfonyloxy)-5H-[1,2,4]triazolo[4,3-a]quinazolin-4-ylmethyl)-benzoate To a stirred solution of 7.9 g (24.3 mmol) of the compound obtained in Step 2 in 100 ml of DMF were added 7.93 g (24.3 mmol) of cesium carbonate, and then 5.56 g (24.3 mmol) of methyl 4-(bromomethyl)benzoate. The mixture was stirred overnight and the solvent was removed under vacuum. The resulting residue was partitioned between $H_2O$ and a mixture of dichloromethane and ethyl acetate. A first portion (5.9 g) of product insoluble in the two phases was obtained by filtration then recrystallized in methanol to give 4.85 g of the pure title compound. The organic phase was separated, washed with water and brine, and dried over anhydrous sodium sulfate. Concentration under reduced pressure afforded 4.5 g of crude product that was recrystalized in methanol to provide 2.2 g of pure compound. An additional portion of 2.5 g was finally obtained after column chromatography on silica gel of the residues gathered from the organic phases (dichloromethane/methanol 98/2 v/v). All in all, 9.55 g (yield: 81.5%) of the desired product were obtained.

TLC: $CH_2Cl_2/CH_3OH$ 95/5 v/v Rf=0.35

Preparation D: 4-(5-oxo-7-(Trifluoromethylsulfonyloxy)-5H-[1,2,4]triazolo[4,3-a]quinazolin-4-ylmethyl)-benzoic acid Step 1: tert-Butyl 4-(5-oxo-7-(Trifluoromethylsulfonyloxy)-5H-[1,2,4]triazolo[4,3-a]quinazolin-4-ylmethyl)-benzoate The product is obtained with a yield of 60.5% (0.95 g) according to the procedure of Step 3 of Preparation C using 1.0 g (2.99 mmol) of compound obtained in Step 1 of Preparation C and 0.81 g (2.99 mmol) of tert-butyl-4-(bromomethyl)benzoate.

Step 2: 4-(5-oxo-7-(Trifluoromethylsulfonyloxy)-5H-[1,2,4]triazolo[4,3-a]quinazolin-4-ylmethyl)-benzoic acid To a suspension of 0.27 g (0.515 mmol) of compound obtained in Step 1 in 30 ml of dichloromethane, 2.7 ml of trifluoroacetic acid were added and stirring was continued at room temperature for 16 hours. The reaction mixture was poured into water and the resulting mixture stirred for 15 minutes. The ensuing precipitate was filtered off, washed with water until neutral pH and dried at 50° C. under vacuum to provide 0.21 g of the desired product.

TLC: dichloromethane/methanol 90/10 v/v Rf=0.30

Example 1

Methyl 4-{6-[3-(4-methoxyphenyl)-prop-1-ynyl]-1-methyl-2,4-dioxo-1,4-dihydro-2H-quinazolin-3-ylmethyl}-benzoate To a stirred suspension of 1.5 g (3.33 mmol) of compound obtained in Step 3 of Preparation A in 110 ml of triethylamine were added, under nitrogen atmosphere, 0.6 g (4 mmol) of 3-(4-methoxyphenyl)-prop-1-yne (described in the literature: *J. Prakt. Chem.*, 1966, 33, 84–95) in 10 ml of triethylamine, 47 mg (0.06 mmol) of dichlorobis (triphenylphosphine)palladium(II) and 26 mg (0.13 mmol) of CuI. The mixture was heated to 60° C. over 3 hours (uncomplete reaction). The mixture was then concentrated under vacuum and the residue purified by flash chromatography to afford 0.130 mg of the desired product (yield: 6%) which was crystallized in a mixture of dichloromethane/methanol.

TLC: $CH_2Cl_2$/Acetone 99/1 v/v Rf=0.9

N.M.R: DMSO $^1$H δ (ppm); 3.5 (s, 3H); 3.75 (s, 3H); 3.8 (s, 5H); 5.2 (s, 2H); 6.9 (d, 2H); 7.35 (s, 2H); 7.45 (m, 3H); 7.85 (d, 1H); 7.9 (d, 2H); 8.0 (s, 1).

IR: 2361, 1702, 1656, 1612, 1508, 1475, 1279, 1249, 117, 1102, 958, 805 cm$^{-1}$

Mp=168.5° C.

Purity (HPLC): 97.9%

Example 2

4-[1-Methyl-2,4-dioxo-6-(3-phenyl-prop-1-ynyl)-1,4-dihydro-2H-quinazolin-3-ylmethyl]-benzoic acid To a stirred solution of 0.68 g (1.56 mmol) of compound obtained in Step 4 of Preparation A in 6.8 ml of dry DMF, were added successively, under nitrogen atmosphere, 1.2 ml (0.8 g, 6.24 mmol) of diisopropylethylamine, 56.8 mg (0.078 mmol) of dichlorobis (triphenylphosphine)palladium (II), a catalytic amount of CuI and 0.273 ml (0.253 g, 2.18 mmol) of 3-phenyl-1-propyne. The reaction mixture was heated to 50° C. over approximately 4 hours. Then, the mixture is concentrated under vacuum and the residue purified by flash chromatography (dichloromethane/MeOH 90/10 v/v) to afford, after crystallization in a mixture of dichloromethane/ether, 0.270 g of the desired product (yield: 40.8%).

TLC: $CH_2Cl_2$/MeOH 9/1 v/v Rf=0.50

N.M.R: DMSO $^1$H δ (ppm); 3.5 (s, 3H); 3.9 (s, 2H); 5.2 (s, 2H); 7.20–7.50 (m, 8H); 7.80 (m, 3H); 8.05 (s, 1H); 12.8 (bs, 1H);

IR: 2894, 1700, 1660, 1616, 1508,1314, 1295, 1097, 825, 795, 747 cm$^{-1}$

Mp=258° C.

Purity (HPLC): 98.6%

Example 3

4-{6-[3-(4-Methoxy-phenyl)-prop-1-ynyl]-1-methyl-2,4-dioxo-1,4-dihydro-2H-quinazolin-3-ylmethyl}-benzoic acid This compound was obtained according to the procedure described in Example 2 using as reagent 3-(4-methoxyphenyl)-prop-1-ynyl. The crude product was crystallized in dioxane to afford the desired compound.

TLC: $CH_2Cl_2$/MeOH 9/1 v/v Rf=0.50

N.M.R: DMSO $^1$H δ (ppm); 3.55 (s, 3H); 3.75 (s, 3H); 3.8 (s, 2H); 5.15 (s, 2H); 6.9 (d, 2H); 7.30 (d, 2H); 7.40 (m, 3H); 7.85 (m, 3H); 8.00 (s, 1H); 12.85 (bs, 1H);

IR: 2646, 1687, 1659, 1508, 1477, 1422, 1325, 1242, 1177, 1040, 950, 812 cm$^{-1}$

Mp=262° C.

Purity (HPLC): 95.4%

Example 4

4-[1-Methyl-2,4-dioxo-6-(3-phenyl-prop-1-ynyl)-1,4-dihydro-2H-pyrido[3,4-d]pyrimidin-3-ylmethyl]-benzoic acid To a stirred solution of 0.1 g (0.22 mmol) of the compound of Preparation B in 1 ml of dry DMF were added successively 0.2 ml (0.14 g, 1.1 mmol) of diisopropylethylamine, 9 mg (0.012 mmol) of dichlorobis (triphenylphosphine)palladium(II), a catalytic amount of CuI and 0.046 ml (0.043 g, 1.1 mmol) of 3-phenyl-1-propyne. The reaction was stirred overnight at room temperature and then $H_2O$ and $CH_2Cl_2$ were added. The organic layer was separated and washed with HCl 10% and $H_2O$, then dried over sodium sulfate and concentrated under vacuum. The residue was crystallized in a mixture of dichloromethane/ether to afford 0.040 g of the desired product (yield : 43%).

TLC: CH$_2$Cl$_2$/MeOH 9/1 v/v Rf=0.50
N.M.R: DMSO $^1$H δ (ppm); 3.6 (s, 3H); 3.95 (s, 2H); 5.2 (s, 2H); 7.20–7.50 (m, 7H); 7.80–7.95 (m, 2H); 7.95 (s, 1H); 8.90 (s, 1H); 12.8 (bs, 1).
IR: 1720, 1695, 1678, 1612, 1490, 1279, 1100, 759, 732 cm$^{-1}$
Mp=236.2° C.
Purity (HPLC): 96.7%

Example 5

4-{6-[3-(4-Methoxy-phenyl)-prop-1-ynyl]-1-methyl-2,4-dioxo-1,4-dihydro-2H-pyrido[3,4-d]pyrimidin-3-ylmethyl}-benzoic acid The compound is obtained according to the procedure described in Example 4 using the compound of Preparation B and the 3-(4-methoxyphenyl)-prop-1-yne.
TLC: CH$_2$Cl$_2$/MeOH 9/1 v/v Rf=0.60
N.M.R: DMSO $^1$H δ (ppm); 3.60 (s, 3H); 3.75 (s, 3H); 3.85 (s, 2H); 5.20 (s, 2H); 6.9–7.0 (m, 2H); 7.30–7.40 (m, 2H); 7.45–7.50 (m, 2H); 7.80–7.90 (m, 3H); 8.90 (s, 1H); 12.9 (bs, 1).
IR: 1721, 1670, 1511, 1477, 1421, 1325, 1245, 1178, 1037,792 cm$^{-1}$
Mp=262° C.
Purity (HPLC): 95.9%

Example 6

4-Benzyl-7-(3-phenyl-prop-1-ynyl)-4H-[1,2,4]triazolo[4,3-a]quinazolin-5-one

To a suspension of 1.5 g (3.53 mmol) of compound obtained in Step 1 of Preparation C in 12 ml of DMF were added, under inert atmosphere of nitrogen, 0.574 g (4.94 mmol) of 3-phenylprop-1-yne, 1.45 g (14.4 mmol) of triethylamine and 0.1 g of dichlorobis (triphenylphosphin) palladium(II). The reaction mixture was then stirred and heated at 50° C. for 5 hours. After cooling at room temperature, H$_2$O was added and the mixture extracted several times with AcOEt. The organic phase was washed with water and brine and then dried (Na$_2$SO$_4$) and concentrated, leaving 1.5 g of crude solid that was chromatographied on a silica column (CH$_2$Cl$_2$/CH$_3$OH 98.5/1.5 v/v) to afford 0.25 g (yield: 18%) of an off-white solid pure in TLC. A sample was purified by recrystallization in methanol.
Mp=238° C.
N.M.R DMSO $^1$H δ (ppm): 3.85 (s, 2H); 5.55 (s, 2H); 7.25–7.45 (m, 8H); 7.6 (d, 1H); 7.65–7.75 (m, 2H); 7.85 (d, 1H); 8.5 (s, 1H); 8.7 (s, 1H).

Example 7

4-Benzyl-7-[(4-methoxyphenyl)-prop-1-ynyl]-4H-[1,2,4]-triazolo[4,3-a]quinazolin-5-one The compound was obtained according to the procedure described in Example 6 using the same substrate (Preparation C, Step 1) and 0.48 g of 3-(4-methoxyphenyl)-prop-1-yne. The crude product was purified by chromatography on a silica column (CH$_2$Cl$_2$/CH$_3$OH 98/2 v/v). A treatment of the resultant solid with boiling AcOEt gave 0.15 g (yield: 15%) of an off-white solid pure in TLC.
Mp=267° C.
N.M.R: CDCl$_3$ $^1$H δ (ppm): 3.8 (s, 2H); 3.8 (s, 3H); 5.5 (s, 2H); 6.9 (d, 2H); 7.2–7.35 (m, 5H); 7.6 (d, 1H); 7.68 (d, 2H); 7.8 (d, 1H); 8.4 (s, 1H); 8.7 (s, 1H).

Example 8

Methyl 4-{7-[3-(4-methoxy-phenyl)-prop-1-ynyl]-5-oxo-5H-[1,2,4]triazolo[4,3-]quinazolin-4-ylmethyl}-benzoate The compound was obtained according to the procedure described in Example 6 using the compound of the Preparation C Step 3, 1.1 g of 3-(4-methoxyphenyl)prop-1-yne, and 2.72 g of N-ethyl-N,N-diisopropylamine. The crude product was purified by chromatography on a silica column (CH$_2$Cl$_2$/CH$_3$OH 98/2 v/v). A treatment of the resultant solid with boiling AcOEt gave 1.5 g (yield: 59%) of an off-white solid pure in TLC.
Mp=249° C.
N.M.R: CDCl$_3$ $^1$H δ (ppm): 3.79 (s, 2H); 3.81 (s, 3H); 3.88(s, 3H); 5.56 (s, 2H); 6.89 (d, 2H); 7.30 (d, 2H); 7.60 (d, 1H); 7.70 (d, 2H); 7.82 (d, 1H); 7.97 (d, 2H); 8.44 (s, 1H); 8.7 (s, 1H).

Example 9

4-[5-Oxo-7-(3-phenyl-prop-1-ynyl)-5H-[1,2,4]triazolo[4,3-a]quinazolin-4-ylmethyl]-benzoic acid The compound was obtained according to the procedure described in Example 6 using the compound of the Preparation D (0.195 g), 0.067 g of 3-phenylprop-1-yne, and 0.215 g of N-ethyl-N,N-diisopropylamine. The crude product was purified by chromatography on a silica column (CH$_2$Cl$_2$/CH$_3$OH 90/10 then 85/15 v/v) to afford 0.14 g (yield : 77%) of an off-white solid pure in TLC corresponding to the desired product.
Mp=262° C.
N.M.R: DMSO $^1$H δ (ppm): 3.96 (s, 2H); 5.42 (s, 2H); 7.27 (t, 1H); 7.37 (t, 2H); 7.44 (d, 2H); 7.52 (d, 2H); 7.87 (d, 2H); 8.02 (d, 1H); 8.18–8.22 (m, 2H); 9.53 (s, 1H); 12.5–13.2 (m, 1H).

Example 10

4-(1-Methyl-2,4-dioxo-6-(2-phenylethynyl)-1,4-dihydro-2H-quinazolin-3-ylmethyl)-benzoic acid The compound was obtained according to the procedure described in Example 5 using the compound of the Preparation A Step 4 (0.59 g, 1.35 mmol), 0.193 g (1.89 mmol) of 1-phenyleth-1-yne, 0.050 g of dichlorobis (triphenylphosphine)palladium, a catalytic amount of CuI and 0.700 g (5.4 mmol) of N-ethyl-N,N-diisopropylamine. The crude product was purified by crystallization in dichloromethane provided 0.55 g (yield 100%) of an off-white solid pure in TLC.
Mp=260° C.
N.M.R: DMSO $^1$H δ (ppm): 3.55 (s, 3H); 5.21 (s, 2H); 7.36–7.50 (m, 5H); 7.50–7.65 (m, 3H); 7.82–7.99 (m, 3H); 8.16 (s, 1H); 12.7–13.1 (m, 1H).

Example 11

3-(3,4-Difluoro-benzyl)-1-methyl-6-(3-phenyl-prop-1-ynyl)-1H-quinazoline-2,4-dione
Step 1: 6-Iodo-1-methyl-1H-quinazoline-2,4-dione
20.0 g (72.2 mmol) of 5-iodo-2-methylamino-benzoic acid and 70 ml of acetic acid are introduced into a round-bottomed flask. 11.7 g (144.0 mmol) of potassium isocyanate is added. The mixture is maintained at 80–85° C. for 18 hours before cooling to room temperature. The product is precipitated with the addition of water and filtered. The product is reslurried in hot ethyl acetate and filtered. The product is obtained as follows:
Weight: 12.3 g Yield: 77%
MS: m/z (APCI, AP+) 302.9 [M⁻]⁺
N.M.R: DMSO ¹H δ (ppm): 3.38 (s, 3H); 7.23 (m, 1H); 8.02 (m, 1H), 8.17 (1H, m).

Step 2: 3-(3,4-Difluoro-benzyl)-6-iodo-1-methyl-1H-quinazoline-2,4-dione 0.5 g (1.6 mmol) of 6-Iodo-1H-quinazoline-2,4-dione from the preceding stage is dissolved in 10 ml of dimethylformamide and 1.0 g (3.2 mmol) of cesium carbonate is added. The mixture is stirred 10 minutes before adding 3,4-di-fluorobenzyl bromide 0.38 g (1.8 mmol). Stirring is continued overnight at room temperature. Water (30 ml) is added and the product is filtered. Slurried solid product in hot ethyl acetate and filtered to obtain:
Weight: 0.49 g Yield: 68%
MS: m/z (APCI, AP+) 429.0 [M⁻]⁺
CHN Analysis: $C_{16}H_{11}F_2IN_2O_2 \cdot 0.13\ H_2O$
Calcd: C, 44.64; H, 2.65; N, 6.51.
Found: C, 44.25; H, 2.35; N, 6.32.

Step 3: 3-(3,4-Difluoro-benzyl)-1-methyl-6-(3-phenyl-prop-1-ynyl)-1H-quinazoline-2,4-dione To 0.45 g (1.1 mmol) 3-(3,4-Difluoro-benzyl)-6-iodo-1-methyl-1H-quinazoline-2,4-dione and 0.56 g (4.4 mmol) di-isopropyl ethylamine in 15 ml DMF is added bis-triphenylphosphine palladium di-chloride (catalytic) followed by CuI (catalytic). 0.18 g (1.3 mmol) 3-phenyl-propyne is added and the mixture is heated to 70° C. for 6 hours. The mixture is allowed to cool to room temperature and stirred overnight. Water is added and the mixture stirred 30 minutes. Filtered and triturated solid in hot EtOAc and filtered. Purified by flash chromatography (EtOAc/hexane eluent).
Weight: 0.13 g Yield: 8%
MS: m/z (APCI, AP+) 417.2 [M⁻]⁺
CHN Analysis: $C_{25}H_{18}F_2N_2O_2 \cdot 0.54H_2O$
Calcd: C, 70.46; H, 4.51; N, 6.57.
Found: C, 70.07; H, 4.36; N, 6.58.

Example 12

3-(3,4-Difluoro-benzyl)-6-[3-(4-fluoro-phenyl)-prop-1-ynyl]-1-methyl-1H-quinazoline-2,4-dione Step 1: 1-(4-Fluoro-phenyl)-prop-2-yn-1-ol A −78° C. solution of 4-fluorobenzaldehyde 5.0 g (40.3 mmol) in 20 ml THF is treated dropwise with a solution of alkynyl magnesium chloride (48.1 mmol, 96.3 ml of a 0.5 M solution in THF). After the addition is complete the mixture is allowed to warm to room temperature and stirred overnight. Saturated aqueous NH₄Cl is added and the product extracted with 1:1 EtOAc/Et₂O (2×). The organic extracts were combined and washed with saturated aqueous NaCl solution, then dried (MgSO₄). Purified by flash chromatography with 5% EtOAc/hexane eluent to obtain a yellow oil.
Weight: 4.8 g Yield: 80%
MS: m/z (APCI, AP+) 151.1 [M⁻]⁺
N.M.R: CDCl₃ ¹H δ (ppm): 2.41 (1H, d, J=6.1); 2.68 (1H, d, J=2.2); 5.45 (1H, m), 7.03–7.09 (2H, m); 7.50–7.56 (1H, m).

Step 2: 1-Fluoro-4-prop-2-ynyl-benzene

To a solution of 4.7 g (31.3 mmol) 4-(Fluoro-phenyl)-prop-2-yn-1-ol in CH₂Cl₂ (20 ml) cooled to −78° C. is added 4.4 g (37.6 mmol) Et₃SiH in one portion followed by 5.3 g (37.6 mmol) BF₃.Et₂O dropwise over 2 minutes. The solution was warmed briefly to −20° C. and then re-cooled to −78C and stirred 1 hour. The mixture is then allowed to warm to room temperature and stirred 1 hour. Saturated aqueous NH₄Cl is added and the solution extracted with EtOAc (2×). The organic extracts are combined and washed with saturated aqueous NaCl solution and dried (MgSO₄). Purify by flash chromatography (EtOAc/hexane eluent).
Weight: 3.1 g Yield: 74%
MS: m/z (APCI, AP+) 135.1 [M⁻]⁺
N.M.R: CDCl₃ ¹H δ (ppm):) 2.19 (1H, m); 2.68 (1H, d, J=2.2); 3.57 (2H, m), 7.01–7.09 (2H, m); 7.29–7.33 (2H, m).

Step 3: 3-(3,4-Difluoro-benzyl)-6-[3-(4-fluoro-phenyl)-prop-1-ynyl]-1-methyl-1H-quinazoline-2,4-dione To 0.5 g (1.06 mmol) 3-(3,4-Difluoro-benzyl)-6-iodo-1-methyl-1H-quinazoline-2,4-dione and 0.52 g (4.2 mmol) di-isopropyl ethylamine in 15 ml DMF is added bis-triphenylphosphine palladium di-chloride (catalytic) followed by CuI (catalytic). 0.15 g (1.3 mmol) 1-fluoro-4-prop-2-ynyl-benzene is added and the mixture is heated to 70° C. for 6 hours. The mixture is allowed to cool to room temperature and stir overnight. Water is added and the mixture stirred 30 minutes. Filtered and triturated solid in hot EtOAc and filtered. Purified by flash chromatography (EtOAc/hexane eluent).
Weight: 0.075 g Yield: 36%
MS: m/z (APCI, AP+) 435.2 [M⁻]⁺
CHN Analysis: Calcd: C, 69.12; H, 3.94; N, 6.45. Found: C, 68.82; H, 3.59; N, 6.12.

Example 13

3-(4-Bromo-benzyl)-1-methyl-6-(3-phenyl-prop-1-ynyl)-1H-quinazoline-2,4-dione

Step 1: 3-(4-Bromo-benzyl)-6-iodo-1-methyl-1H-quinazoline-2,4-dione 0.5 g (1.6 mmol) of 6-Iodo-1-methyl-1H-quinazoline-2,4-dione from Example 1 Step 1 is dissolved in 10 ml of dimethylformamide and 1.0 g (3.2 mmol) of cesium carbonate is added. The mixture is stirred 10 minutes before adding 4-bromobenzyl bromide 0.45 g (1.8 mmol). Stirring is continued overnight at room temperature. Water (30 ml) is added and the product is filtered. Slurried solid product in hot ethyl acetate and filtered to obtain:
Weight: 0.52 g Yield: 69%
MS: m/z (APCI, AP+) 470.9 [M⁻]⁺
CHN Analysis: Calcd: C, 40.79; H, 2.57; N, 5.95. Found: C, 40.43; H, 2.41; N, 5.89.

Step 2: 3-(4-Bromo-benzyl)-1-methyl-6-(3-phenyl-prop-1-ynyl)-1H-quinazoline-2,4-dione To 0.50 g (1.06 mmol) 3-(4-Bromo-benzyl)-6-iodo-1-methyl-1H-quinazoline-2,4-dione and 0.54 g (4.2 mmol) di-isopropyl ethylamine in 15 ml DMF is added bis-triphenylphosphine palladium di-chloride (catalytic) followed by CuI (catalytic). 0.15 g (1.3 mmol) 3-phenyl-propyne is added and the mixture is heated to 70° C. for 6 hours. The mixture is allowed to cool to room temperature and stir overnight. Water is added and the mixture stirred 30 minutes. Filtered and triturate solid in hot EtOAc and filter. Dissolve in THF and filter through a plug of silica gel with THF eluent. Triturate solid in hot EtOAc and filter.
Weight: 0.11 g Yield: 23%
MS: m/z (APCI, AP+) 461.2 [M⁻]⁺
CHN Analysis: Calcd: C, 65.37; H, 4.17; N, 6.10. Found: C, 65.66; H, 4.09; N, 6.08.

Example 14 tert-Butyl 4-[6-(3-biphenyl-4-yl-prop-1-ynyl)-1-methyl-2,4-dioxo-1,4-dihydro-2H-quinazolin-3-ylmethyl]-benzoate Step 1: tert-butyl 4-(6-iodo-1-methyl-2,4-dioxo-1,4-dihydro-2H-quinazolin-3-ylmethyl)-benzoate 7.8 g (25.8 mmol) of 6-Iodo-1-methyl-1H-quinazoline-2,4-dione from Example 11 Step 1 is dissolved in 60 ml of dimethylformamide and 9.8 g (30.1 mmol) of cesium carbonate is added. The mixture is stirred 10 minutes before adding 4-bromomethyl-benzoic acid tert-butyl ester 8.4 g (30.1 mmol). Stirring is continued overnight at room temperature. Water (100 ml) is added and the product is filtered. Slurried solid product in hot ethyl acetate and filtered to obtain:

Weight: 7.1 g Yield: 56%
MS: m/z (APCI, AP+) 437.0 (492-tert-butyl) [M$^-$]$^+$
CHN Analysis: Calcd: C, 51.23; H, 4.40; N, 5.69. Found: C, 51.13; H, 4.32; N, 6.04.

Step 2: 1-Biphenyl-4-yl-prop-2-yn-1-ol

A −78° C. solution of 4-phenylbenzaldehyde 5.0 g (27.4 mmol) in 20 ml THF is treated dropwise with a solution of alkynyl magnesium chloride (60.0 mmol, 120 ml of a 0.5 M solution in THF). After the addition is complete the mixture is allowed to warm to room temperature and stir overnight. Saturated aqueous NH$_4$Cl is added and the product extracted with 1:1 EtOAc/Et$_2$O (2x). The organic extracts were combined and washed with saturated aqueous NaCl solution, then dried (MgSO$_4$). Purified by flash chromatography with EtOAc/hexane eluent followed by crystallization from EtOAc/hexane to obtain a white solid.

Weight: 4.6 g Yield: 81%
MS: m/z (APCI, AP+) 149.0 [M$^-$]$^+$
CHN Analysis: Calcd: C, 86.51; H, 5.81. Found: C, 86.11; H, 5.77.

Step 3: 4-Prop-2-ynyl-biphenyl

To a solution of 3.0 g (14.4 mmol) 1-biphenyl-4-yl-prop-2-yn-1-ol in CH$_2$Cl$_2$ (20 ml) cooled to −78° C. is added 2.2 g (18.7 mmol) Et$_3$SiH in one portion followed by 2.7 g (18.7 mmol) BF$_3$.Et$_2$O dropwise over 2 minutes. The solution was warmed briefly to −20° C. and then re-cooled to −78 C and stirred 1 hour. The mixture is then allowed to warm to room temperature and stir 1 hour. Saturated aqueous NH$_4$Cl is added and the solution extracted with EtOAc (2x). The organic extracts are combined and washed with saturated aqueous NaCl solution and dried (MgSO$_4$). Purify by flash chromatography (EtOAc/hexane eluent). Obtain low melting solid.

Weight: 0.5 g Yield: 18%
MS: m/z (APCI, AP+) 191.1 [M$^-$]$^+$

Step 4: tert-butyl 4-[6-(3-biphenyl-4-yl-prop-1-ynyl)-1-methyl-2,4-dioxo-1,4-dihydro-2H-quinazolin-3-ylmethyl]-benzoate To 0.50 g (1.0 mmol) 4-(6-Iodo-1-methyl-2,4-dioxo-1,4-dihydro-2H-quinazolin-3-ylmethyl)-benzoic acid tert-butyl ester and 0.52 g (4.0 mmol) di-isopropyl ethylamine in 15 ml DMF is added bis-triphenylphosphine palladium di-chloride (catalytic) followed by CuI (catalytic). 0.25 g (1.3 mmol) 4-prop-2-ynyl-biphenyl is added and the mixture is heated to 70° C. for 6 hrs. The mixture is allowed to cool to room temperature and stir overnight. Water is added and the mixture stirred 30 minutes. Filtered and triturate solid in hot EtOAc and filter. Dissolve in THF and filter through a plug of silica gel with THF eluent. Triturate solid in hot EtOAc and filter Weight: 0.21 g Yield: 38%
MS: m/z (APCI, AP+) 555.2 [M$^-$]$^-$
CHN Analysis: Calcd: C, 77.68; H, 5.79; N, 5.03. Found: C, 77.68; H, 5.62; N, 4.78.

Example 15 tert-Butyl 4-{6-[3-(4-fluoro-phenyl)-prop-1-ynyl]-1-methyl-2,4-dioxo-1,4-dihydro-2H-quinazolin-3-ylmethyl}-benzoate To 1.0 g (2.0 mmol) 3-(3,4-Difluoro-benzyl)-6-iodo-1-methyl-1H-quinazoline-2,4-dione from Example 14 Step 1 and 1.0 g (8.4 mmol) di-isopropyl ethylamine in 15 ml DMF is added bis-triphenylphosphine palladium di-chloride (catalytic) followed by CuI (catalytic). 0.44 g (3.3 mmol) 1-fluoro-4-prop-2-ynyl-benzene is added and the mixture is heated to 70° C. for 6 hrs. The mixture is allowed to cool to room temperature and stir overnight. Water is added and the mixture stirred 30 minutes. Filtered and dry under reduced pressure.

Weight: 0.11 g Yield: 11%
MS: m/z (APCI, AP+) 497.2 [M$^-$]$^-$
CHN Analysis: Calcd: C, 72.28; H, 5.46; N, 5.62. Found: C, 72.38; H, 5.83; N, 5.29.

Example 16

4-(6-{3-[4-(tert-Butyl-dimethyl-silanyloxy)-phenyl]-prop-1-ynyl}-1-methyl-2,4-dioxo-1,4-dihydro-2H-quinazolin-3-ylmethyl)-benzoic acid Step 1: 4-(tert-Butyl-dimethyl-silanyloxy)-benzaldehyde 3.0 g (24.5 mmol) of 4-hydroxy-benzaldehyde in 20 ml THF is treated with 4.8 g (31.9 mmol) tert-Butyl-chlorodimethyl-silane followed by 6.2 g (47.8 mmol) di-isopropyl ethylamine and imidazole (catalytic). The resulting mixture is stirred overnight at room temperature. Dilute with 1:1 EtOAc/Et$_2$O and wash with saturated aqueous NaHCO$_3$ solution, saturated aqueous NaCl (3x), and dried (MgSO$_4$). Purify by flash chromatography (EtOAc/hexane eluent).

Weight: 4.8 g Yield: 83%
MS: m/z (APCI, AP+) 263.0 [M$^-$]$^+$
N.M.R: CDCl$_3$ $^1$H δ (ppm): 0.0 (6H, s); 0.75 (9H, s); 6.67–6.71 (2H, m); 7.52–7.56 (2H, m); 9.64 (1H, s).

Step 2: 1-[4-(tert-Butyl-dimethyl-silanyloxy)-phenyl]-prop-2-yn-1-ol

A −78° C. solution of 4-(tert-Butyl-dimethyl-silanyloxy)-benzaldehyde 3.3 g (13.9 mmol) in 20 ml THF is treated dropwise with a solution of alkynyl magnesium chloride (18.2 mmol, 36.4 ml of a 0.5 M solution in THF). After the addition is complete the mixture is allowed to warm to room temperature and stir overnight. Saturated aqueous NH$_4$Cl is added and the product extracted with 1:1 EtOAc/Et$_2$O (2x). The organic extracts were combined and washed with saturated aqueous NaCl solution, then dried (MgSO$_4$). Purified by flash chromatography with EtOAc/hexane eluent followed by crystallization from EtOAc/hexane to obtain a white solid.

Weight: 3.1 g Yield: 85%
N.M.R: CDCl$_3$ $^1$H δ (ppm): 0.0 (6H, s); 0.78 (9H, s); 1.89 (1H, d, J=6.1); 2.46 (1H, d, J=2.2); 5.21–5.22 (1H, m); 6.62–6.66 (2H, m); 7.20–7.24 (2H, m).

Step 3: tert-Butyl-dimethyl-(4-prop-2-ynyl-phenoxy)-silane

To a solution of 3.0 g (11.4 mmol) 1-[4-(tert-Butyl-dimethyl-silanyloxy)-phenyl]-prop-2-yn-1-ol in CH$_2$Cl$_2$ (20 ml) cooled to −78° C. is added 1.6 g (13.7 mmol) Et$_3$SiH in one portion followed by 1.9 g (13.7 mmol) BF$_3$.Et$_2$O dropwise over 2 minutes. The solution was warmed briefly to −20° C. and then re-cooled to −78° C. and stirred 2.5 hours. The mixture is then allowed to warm to room temperature and stir 1 hour. Saturated aqueous $NH_4Cl$ is added and the solution extracted with EtOAc (2×). The organic extracts are combined and washed with saturated aqueous NaCl solution and dried ($MgSO_4$). Purify by flash chromatography (EtOAc/hexane eluent). Yellow oil.
Weight: 0.57 g Yield: 20%
MS: m/z (APCI, AP+) 247.0 $[M^-]^+$
N.M.R: $CDCl_3$ $^1H$ δ (ppm):) 0.0 (6H, s); 0.79 (9H, s); 1.98 (1H, m); 3.35 (2H, m); 6.58–6.62 (2H, m); 7.00–7.02 (2H, m).

Step 4: 4-(6-{3-[4-(tert-Butyl-dimethyl-silanyloxy)-phenyl]-prop-1-ynyl}-1-methyl-2,4-dioxo-1,4-dihydro-2H-quinazolin-3-ylmethyl)-benzoic acid To 0.65 g (1.5 mmol) 4-(6-Iodo-1-methyl-2,4-dioxo-1,4-dihydro-2H-quinazolin-3-ylmethyl)-benzoic acid and 0.77 g (6.0 mmol) di-isopropyl ethylamine in 15 ml DMF is added bis-triphenylphosphine palladium di-chloride (catalytic) followed by CuI (catalytic). 0.5 g (2.0 mmol) tert-Butyl-dimethyl-(4-prop-2-ynyl-phenoxy)-silane is added and the mixture is heated to 70° C. for 6 hours. The mixture is allowed to cool to room temperature and stir overnight. Water is added and the mixture stirred 30 minutes. Filter and dry under reduced pressure. Purify by flash chromatography (EtOAc/hexane eluent)
Weight: 0.097 g Yield: 12%
MS: m/z (APCI, AP+) 555.3 $[M^-]^+$
CHN Analysis: $C_{32}H_{34}N_2O_5Si.0.21H_2O$ Calcd: C, 68.82; H, 6.21; N, 5.02. Found: C, 68.42; H, 6.14; N, 4.97.

Example 17

Methyl 4-[1-methyl-2,4-dioxo-6-(3-phenyl-prop-1-ynyl)-1,4-dihydro-2H-quinazolin-3-ylmethyl]-benzoate Step 1: Methyl 4-[(5-iodo-2-methylamino-benzoylamino)-methyl]-benzoate To 13.4 g (48.3 mmol) 5-Iodo-2-methylamino-benzoic acid 11.1 g (57.9 mmol) EDAC-HCl, 7.8 g (57.9 mmol) HOBT, and di-isopropyl ethylamine 7.5 g (57.9 mmol) in 200 ml ⁻DMF is treated with 11.7 g (57.9 mmol) 4-aminomethyl-benzoic acid methyl ester hydrochloride. The resulting mixture is stirred overnight at room temperature before diluting with water and stirring 20 minutes. The solid is filtered and then triturated in hot EtOAc, cooled and filtered.
Weight: 14.5 g Yield: 71%
MS: m/z (APCI, AP+) 424.2 $[M^-]^+$
N.M.R: DMSO $^1H$ δ (ppm): 2.7 (3H, d, J=4.8); 3.80 (3H, s); 4.43 (2H, d, J=5.8); 6.46 (1H, m); 7.39–7.41 (2H, m); 7.51–7.54 (1H, m); 7.73–7.74 (1H, m); 7.86–7.90 (3H, m); 9.03 (1H, m).

Step 2: Methyl 4-(6-iodo-1-methyl-2,4-dioxo-1,4-dihydro-2H-quinazolin-3-ylmethyl)-benzoate To 3.4 g (8.0 mmol) 4-[(5-Iodo-2-methylamino-benzoylamino)-methyl]-benzoic acid methyl ester in 20 ml THF and 10 ml pyridine is added 2.4 g (8.0 mmol) triphosgene portionwise. After the addition is complete the mixture is heated to reflux for 1.5 hours. Cool and pour onto ice. The solution is made basic with the addition of saturated aqueous $NaHCO_3$. The resulting solid is filtered and triturated in hot EtOAc.
Weight: 2.4 g Yield: 66%
MS: m/z (APCI, AP+) 451.0 $[M^-]^+$
N.M.R: DMSO $^1H$ δ (ppm): 3.30 (3H, s); 3.82 (3H, s); 4.72 (2H, s); 7.09 (1H, d, J=8.79); 7.54–7.57 (2H, m); 7.51–7.54 (1H, m); 7.89–7.93 (2H, m); 8.23 (1H, m).

Step 3: Methyl 4-[1-methyl-2,4-dioxo-6-(3-phenyl-prop-1-ynyl)-1,4-dihydro-2H-quinazolin-3-ylmethyl]-benzoate To 19.6 g (44.9 mmol) 4-(6-Iodo-1-methyl-2,4-dioxo-1,4-dihydro-2H-quinazolin-3-ylmethyl)-benzoic acid methyl ester and 23.2 g (179.6 mmol) di-isopropyl ethylamine in 200 ml DMF is added bis-triphenylphosphine palladium di-chloride (1.0 g, catalytic) followed by CuI (0.4 g, catalytic). 7.3 g (62.9 mmol) 3-phenyl-propyne is added and the mixture is heated to 70° C. for 6 hrs. The mixture is allowed to cool to room temperature and stir overnight. Water is added and the mixture stirred 30 minutes. Filter and dry under reduced pressure. Solid from EtOAc.
Weight: 5.0 g Yield: 27%
MS: m/z (APCI, AP+) 425.1 $[M^-]^+$
CHN Analysis: Calcd: C, 73.96; H, 5.06; N, 6.39. Found: C, 73.60; H, 5.11; N, 6.37.

Example 18

2-Dimethylamino-ethyl 4-[1-methyl-2,4-dioxo-6-(3-phenyl-prop-1-ynyl)-1,4-dihydro-2H-quinazolin-3-ylmethyl]-benzoate A mixture of 0.72 g (1.7 mmol) 4-[1-Methyl-2,4-dioxo-6-(3-phenyl-prop-1-ynyl)-1,4-dihydro-2H-quinazolin-3-ylmethyl]-benzoic acid, 0.43 g (2.2 mmol) EDAC-HCl, 0.29 g (2.2 mmol) HOBT in 10 ml DMF is treated with 0.19 g (2.2 mmol) ethanolamine. The resulting mixture is stirred overnight at room temperature before diluting with water and extracting with 1:1 $EtOAc/Et_2O$ (2×). The combined organic extracts are washed with saturated aqueous NaCl (3×), dried ($MgSO_4$). The resulting oil is dissolved in EtOAc and treated with saturated methanolic HCl. Concentration provided a solid which is triturated in EtOAc and filtered.
Weight: 0.21 g Yield: 23%
MS: m/z (APCI, AP+) 496.2 $[M^-]^+$
CHN Analysis: $C_{30}H_{29}N_3O_4.0.25H_2O$ Calcd: C, 67.16; H, 5.73; N, 7.83. Found: C, 66.77; H, 5.56; N, 7.64.

Example 19

N,N-Dimethyl-4-[1-methyl-2,4-dioxo-6-(3-phenyl-prop-1-ynyl)-1,4-dihydro-2H-quinazolin-3-ylmethyl]-benzamide Step 1: 4-[1-Methyl-2,4-dioxo-6-(3-phenyl-prop-1-ynyl)-1,4-dihydro-2H-quinazolin-3-ylmethyl]-benzoyl chloride To a stirred suspension of 4.0 g (9.4 mmol) of compound obtained in Example 12 in 150 ml of dichloromethane were added, under nitrogen atmosphere, 4 drops of N,N-dimethylformamide and 0.9 mL (10.4 mmol) of oxalyl chloride. The mixture was stirred for 4 hours at room temperature. The suspension had partially cleared. An additional 1.8 mL (20.8 mmol) of oxalyl chloride was added and the reaction went immediately clear. The reaction was stirred for an additional hour and then concentrated under vacuum. The resulting solid was redissolved in diethyl ether and again concentrated in vacuo. The resulting yellowish solid was stored under nitrogen and used without further purification.

Step 2: N,N-Dimethyl-4-[1-methyl-2,4-dioxo-6-(3-phenyl-prop-1-ynyl)-1,4-dihydro-2H-quinazolin-3-ylmethyl]-benzamide To a solution of 0.5 g (1.1 mmol) of compound obtained in Step 1 in 50 ml of dichloromethane, 10 ml of dimethylamine in ether were added and stirring was continued at room temperature for 16 hours. The reaction mixture was partitioned between 1 M HCl and dichloromethane. The organic layer was washed with saturated sodium bicarbonate, dried over magnesium sulfate, filtered, and concentrated to give 0.4 g of the desired product.
N.M.R: CDCl₃ 1H δ (ppm): 8.30 (s, 1H), 7.71 (dd, 1H), 7.53 (d, 2H), 7.41–7.25 (m, 7H), 7.12 (d, 1H), 5.27 (s, 2H), 3.84 (s, 2H), 3.58 (s, 3H), 3.07 (bs, 3H), and 2.94 (bs, 3).
MS: M⁺+1=452.2 Da
Mp=171–173° C.
Purity (HPLC): 100%

Example 20

1-Methyl-6-(3-phenyl-prop-1-ynyl)-3-[4-(piperidine-1-carbonyl)-benzyl]-1H-quinazoline-2,4-dione The compound is obtained, as a white solid, according to the procedure of Example 19, Step 2, but using piperidine.
N.M.R: CDCl₃ ¹H δ (ppm): 8.30 (s, 1H), 7.70 (dd, 1H), 7.53 (d, 2H), 7.41–7.25 (m, 7H), 7.12 (d, 1H), 5.27 (s, 2H), 3.83 (s, 2H), 3.65 (bs, 2H), 3.58 (s, 3H), 3.32 (bs, 2H), and 1.64 (bs, 6).
MS: M⁺+1=492.3 Da
Purity (HPLC): 100%

Example 21

N-Ethyl-4-[1-methyl-2,4-dioxo-6-(3-phenyl-prop-1-ynyl)-1,4-dihydro-2H-quinazolin-3-ylmethyl]-benzamide The compound is obtained, as a white solid, according to the procedure of Example 19, Step 2, but using ethylamine.
N.M.R: DMSO ¹H δ (ppm): 8.37 (bt, 1H), 8.02 (s, 1H), 7.82 (dd, 1H), 7.73 (dd, 2H), 7.46 (d, 1H), 7.41–7.32 (m, 6H), 7.26–7.22 (m, 1H), 5.14 (s, 2H), 3.90 (s, 2H), 3.50 (s, 3H), 3.24 (q, 2H), and 1.08 (t, 3).
MS: M++1=452.3 Da
Purity (HPLC): 100%

Example 22

1-Methyl-3-[4-(4-methyl-piperazine-1-carbonyl)-benzyl]-6-(3-phenyl-prop-1-ynyl)-1H-quinazoline-2,4-dione When in the procedure of Example 19, Step 2, dimethylamine is replaced with N-methyl piperazine, and the reaction is concentrated and triturated with saturated sodium bicarbonate solution, the title compound is obtained as an off-white solid.
N.M.R: CDCl₃ ¹H δ (ppm): 8.30 (s, 1H), 7.70 (dd, 1H), 7.53 (d, 2H), 7.41–7.25 (m, 7H), 7.13 (d, 1H), 5.27 (s, 2H), 3.83 (bs, 4H), 3.58 (s, 3H), 3.48 (bs, 2H), 2.52 (bs, 4H), and 2.36 (s, 3).
MS: M⁺+1=507.3 Da

Example 23

N,N-Bis-(2-hydroxy-ethyl)-4-[1-methyl-2,4-dioxo-6-(3-phenyl-prop-1-ynyl)-1,4-dihydro-2H-quinazolin-3-ylmethyl]-benzamide The compound is obtained according to the procedure of Example 19, Step 2, but using diethanolamine; the title compound is isolated as an off-white solid.
N.M.R: CDCl₃ ¹H δ (ppm): 8.29 (s, 1H), 7.70 (dd, 1H), 7.52 (d, 2H), 7.41–7.25 (m, 7H), 7.12 (d, 1H), 5.26 (s, 2H), 3.94 (bs, 2H), 3.83 (s, 2H), 3.67 (bs, 4H), 3.58 (s, 3H), 3.42 (bs, 2H), and 2.93 (bs, 2H).
Ms: M⁺+1=512.3 Da

Example 24

3-(4-Hydroxymethyl-benzyl)-1-methyl-6-(3-phenyl-prop-1-ynyl)-1H-quinazoline-2,4-dione A solution of 0.5 g (1.1 mmol) of compound obtained in Example 19, Step 1 in 50 ml of tetrahydrofuran, was added dropwise to a suspension of 0.047 g (1.2 mmol) lithium aluminum hydride in 50 ml tetrahydrofuran at 0° C. After complete addition, the off-white suspension was warmed to room temperature and stirring was continued for 4 hours. The reaction mixture was concentrated in vacuum and carefully partitioned between 1 M HCl and ethyl acetate. The organic layer was dried over magnesium sulfate, filtered, and concentrated to give an oily yellow solid. Chromatography (silica, 1:1 ethyl acetate\hexanes) gave 0.25 g of the title compound as a white solid.
N.M.R: CDCl₃ ¹H δ (ppm): 8.30 (s, 1H), 7.69 (dd, 1H), 7.50 (d, 2H), 7.41–7.25 (m, 7H), 7.11 (d, 1H), 5.26 (s, 2H), 4.64 (bs, 2H), 3.84 (s, 2H), 3.57 (s, 3H), and 1.56 (bs, 1).
Ms: M⁺+1=411.2 Da
Mp=161–164° C.
Purity (HPLC): 100%

Example 25

3-(3-Chloro-benzyl)-1-methyl-6-(3-phenyl-propynyl)-1H-quinazoline-2,4-dione

Step 1: 3-(3-Chloro-benzyl)-6-iodo-1-methyl-1H-quinazoline-2,4-dione

To a suspension of 6-iodo-1-methyl-1H-quinazoline-2,4-dione (0.300 g, 0.993 mmol) in 8 ml of DMF was added cesium carbonate (0.971 g, 2.98 mmol). After stirring at room temperature for 30 min, a solution of 3-chlorobenzyl bromide (0.128 ml, 0.993 mmol) in 2 ml of DMF was added dropwise to the reaction mixture and stirred overnight. After 24 h stirring at room temperature, white solids (cesium salt) were filtered and the solution was concentrated. The resulting suspension was diluted with 10 ml of ethyl acetate and filtered again. The filtrate was concentrated and trituration with 10 ml diethyl ether gave 0.25 g (59%) of a white solid.
MP: 164–166° C.
MS(APCI+): m/z 427.0 (MH⁺)
N.M.R: DMSO ¹H δ (ppm): 3.51 (s, 3H, NCH₃), 5.09 (s, 2H, NCH₂Ar), 7.26–7.37 (m, 4H, ArH), 7.37 (s, 1H, ArH), 8.05 (dd, J=8.78, 2.20 Hz, 1H, ArH), 8.27 (d, J=2.20 Hz, 1H, ArH).

Step 2: 3-(3-Chloro-benzyl)-1-methyl-6-(3-phenyl-prop-1-ynyl)-1H-quinazoline-2,4-dione To a mixture of 3-(3-chloro-benzyl)-6-iodo-1-methyl-1H-quinazoline-2,4-dione (0.224 g, 0.525 mmol), CuI (0.010 g, 0.053 mmol) and Pd(PPh₃)₄ (0.030 g, 0.026 mmol), (after purging with nitrogen for 5 min) in 10 ml of anhydrous dioxane was added 3-phenyl-1-propyne (0.098 ml, 0.79 mmol), and followed by diisopropylamine (0.147 ml, 1.05 mmol). Under a nitrogen atmosphere, the reaction mixture was stirred at room temperature for 24 h. After the reaction was completed, ethyl acetate (20 ml) was added and white solids, (H₂N(I—Pr)₂Br) were filtered through celite. The filtrate was concentrated. The product was purified by flash column chromatography on silica gel (20% ethyl acetate:hexane) and concentrated. After stirring at room temperature for 24 h, the reaction mixture was concentrated affording a yellow oil. Trituration with 10 ml of diethyl ether gave 0.200 g (91.7%) of a white solid
MP: 164–166° C.;
Anal. Calcd for C₂₅H₁₉N₂O₂Cl₁: C, 71.23; H, 4.72; N, 6.65. Found: C, 70.85; H, 4.39; N, 6.45.
N.M.R: DMSO ¹H δ (ppm): 3.50 (s, 3H, NCH₃), 3.90 (s, 2H, CCH₂Ar), 5.10 (s, 2H, NCH₂Ar), 7.22–7.47 (m, 10H, ArH), 7.82 (dd, J=8.78, 2.20, 1H, ArH), 8.02 (d, J=2.20 Hz, 1H, ArH); MS(APCI+): m/z 413.1 (MH⁻).

Example 26

3-(3-Fluoro-benzyl)-1-methyl-6-(3-phenyl-prop-1-ynyl)-1H-quinazoline-2,4-dione Step 1: 3-(3-Fluoro-benzyl)-6-iodo-1-methyl-1H-quinazoline-2,4-dione The compound is obtained according to the procedure of Example 25, Step 1, but using 3-fluorobenzyl bromide and the compound obtained in the preceding Step 1.
Weight: 0.30 g; Yield=75%
MP=153–155° C.
MS(APCI+): m/z 408.9 (MH+)
N.M.R: DMSO $^1$H δ (ppm): 3.51 (s, 3H, NCH$_3$), 5.10 (s, 1H, NCH$_2$Ar), 7.05–7.30 (m, 3H, ArH), 7.31–7.35 (m, 2H, ArH), 8.06 (dd, J=8.78, 2.20 Hz, 1H, ArH), 8.26 (d, J=1.95 Hz, 1H, ArH).

Step 2: 3-(3-Chloro-benzyl)-1-methyl-6-(3-phenyl-prop-1-ynyl)-1H-quinazoline-2,4-dione The compound is obtained according to the procedure of Example 25, Step 2, but using 3-phenyl-1-propyne.
Weight: 0.24 g Yield=83%
MP: 143–144° C.
Anal. Calcd for C$_{25}$H$_{19}$N$_2$O$_2$F$_1$: C, 74.09; H, 4.91; N, 6.91.
Found: C, 73.69; H, 4.61; N, 6.78.
N.M.R: DMSO $^1$H δ (ppm): 3.50 (s, 3H, NCH$_3$), 3.90 (s, 2H, CCH$_2$Ar), 5.12 (s, 2H, NCH$_2$Ar), 7.14–7.41 (m, 9H, ArH), 7.46 (d, J=8.54 Hz, 1H, ArH), 7.81 (dd, J=8.78, 1.95 Hz, 1H, ArH), 8.02 (d, J=2.20 Hz, 1H, ArH); MS(APCI+): m/z 397.1 (MH−).

Example 27

3-(4-Chloro-benzyl)-1-methyl-6-(3-phenyl-prop-1-ynyl)-1H-quinazoline-2,4-dione Step 1: 3-(4-Chloro-benzyl)-6-iodo-1-methyl-1H-quinazoline-2,4-dione The compound is obtained according to the procedure of Example 25, Step 1, but using 4-chlorobenzyl bromide.
Weight: 0.40 g Yield=94%
MS(APCI+): m/z 424.9 (MH−)
N.M.R: DMSO $^1$H δ (ppm):) 3.51 (s, 3H, NCH$_3$), 5.08 (s, 1H, NCH$_2$Ar), 7.27–7.34 (m, 4H, ArH), 7.31–7.35 (m, 2H, ArH), 8.06 (dd, J=8.78, 2.20 Hz, 1H, ArH), 8.26 (d, J=2.20 Hz, 1H, ArH).

Step 2: 3-(4-Chloro-benzyl)-1-methyl-6-(3-phenyl-prop-1-ynyl)-1H-quinazoline-2,4-dione The compound is obtained according to the procedure of Example 25, Step 2, but using 3-phenyl-1-propyne and the compound obtained in the preceding Step 1.
Weight: 0.10 g Yield=74%
MP: 175–176° C.
Anal. Calcd for C$_{25}$H$_{19}$N$_2$O$_2$Cl$_1$: C, 70.57; H, 4.33; N, 6.18.
Found: C, 70.86; H, 4.56; N, 6.58
N.M.R: DMSO $^1$H δ (ppm): 3.51 (s, 3H, NCH$_3$), 3.90 (s, 2H, CCH$_2$Ar), 5.09 (s, 2H, NCH$_2$Ar), 7.24–7.47 (m, 10H, ArH), 7.80 (dd, J=6.59, 2.20 Hz, 1H, ArH), 8.02 (d, J=2.20 Hz, 1H, ArH); MS(APCI+): m/z 413.1 (MH−).

Example 28

4-[6-(3-Imidazol-1-yl-prop-1-ynyl)-1-methyl-2,4-dioxo-1,4-dihydro-2H-quinazolin-3-ylmethyl]-benzoic acid; compound with trifluoro-acetic acid The compound is obtained according to the procedure of Example 25, Step 2, but using 1-prop-2-ynyl-1H-imidazole.
Weight: 0.24 g Yield=96%
Purity (HPLC)=98.2%
N.M.R: DMSO $^1$H δ (ppm): 3.52 (s, 3H, NCH$_3$), 5.17 (s, 2H, CCH$_2$Ar), 5.42 (s, 2H, NCH$_2$Ar), 7.40 (d, J=8.30 Hz, 2H, ArH), 7.51 (d, J=8.78 Hz, 2H, ArH), 7.84–7.89 (m, 4H, ArH), 8.14 (d, J=1.95 Hz, 1H, Ar).
MS(APCI+): m/z 415.3 (MH+).

Example 29

3-(3,4-Difluoro-benzyl)-6-(3-imidazol-1-yl-prop-1-ynyl)-1-methyl-1H-quinazoline-2,4-dione Step 1: 3-(3,4-Difluoro-benzyl)-6-iodo-1-methyl-1H-quinazoline-2,4-dione The compound is obtained according to the procedure of Example 25, Step 1, but using 3,4-difluorobenzyl bromide.

Step 2: 3-(3,4-Difluoro-benzyl)-6-(3-imidazol-1-yl-prop-1-ynyl)-1-methyl-1H-quinazoline-2,4-dione The compound is obtained according to the procedure of Example 25, Step 2, but using 1-prop-2-ynyl-1H-imidazole and the compound obtained in the preceding Step 1.
Weight: 0.26 g Yield=93%
MP: 163–165° C.
Purity (HPLC)=98.4%
N.M.R: DMSO $^1$H δ (ppm): 3.50 (s, 3H, NCH$_3$), 5.08 (s, 2H, CCH$_2$Ar), 5.19 (s, 2H, NCH$_2$Ar), 6.96 (s, 1H, ArH), 7.17 (s, 1H, ArH), 7.30–7.41 (m, 3H, ArH), 7.48 (d, J=8.78 Hz, 1H, ArH), 7.81–7.85 (m, 2H, ArH), 8.05 (d, J=2.20 Hz, 1H, ArH).
MS(APCI+): m/z 407.3 (MH+).

Example 30

6-[3-(4-Chloro-phenyl)-prop-1-ynyl]-3-(3,4-difluoro-benzyl)-1-methyl-1H-quinazoline-2,4-dione The compound is obtained according to the procedure of Example 25, Step 2, but using 1-chloro-4-prop-2-ynyl-benzene.
Weight: 0.20 g Yield=63%
MP: 163–165° C.
Purity (HPLC)=99.04%
N.M.R: DMSO $^1$H δ (ppm): 3.50 (s, 3H, NCH$_3$), 3.91 (s, 2H, CCH$_2$Ar), 5.08 (s, 2H, NCH$_2$Ar), 7.17 (s, 1H, ArH), 7.30–7.47 (m, 7H, ArH), 7.82 (dd, J=6.59, 1.95 Hz, 1H, ArH), 8.02 (d, J=1.95 Hz, 2H, ArH).
MS(APCI+): m/z 449.1 (MH+).

Example 31

3-(3-Chloro-benzyl)-6-[3-(4-chloro-phenyl)-prop-1-ynyl]-1-methyl-1H-quinazoline-2,4-dione The compound is obtained according to the procedure of Example 25, Step 2, but using 1-chloro-4-prop-2-ynyl-benzene.
Weight: 0.03 g Yield=31%
MP: 169–171° C.
Anal. Calcd for C$_{25}$H$_{18}$N$_2$O$_2$Cl$_2$: C, 65.44; H, 4.19; N, 6.10.
Found: C, 65.06; H, 3.96; N, 5.89
N.M.R: DMSO $^1$H δ (ppm): 3.50 (s, 3H, NCH$_3$), 3.91 (s, 2H, CCH$_2$Ar), 5.10 (s, 2H, NCH$_2$Ar), 7.30–7.47 (m, 9H, ArH), 7.82 (dd, J=6.34, 2.20 Hz, 1H, ArH), 8.03 (d, J=1.95 Hz, 2H, ArH).
Ms(APCI+): m/z 448.4 (MH+).

Example 32

3-(3,4-Difluoro-benzyl)-1-methyl-6-(3-[1,2,3]triazol-1-yl-prop-1-ynyl)-1H-quinazoline-2,4-dione The compound is obtained according to the procedure of Example 25, Step 2, but using 1-prop-2-ynyl-1H-[1,2,3]triazole.

Weight: 0.20 g Yield=70%
MP: 167–169° C.
Purity (HPLC)=95.2%.
N.M.R: DMSO $^1$H δ (ppm): 3.54 (s, 3H, NCH$_3$), 5.07 (s, 2H, CCH$_2$Ar), 5.62 (s, 2H, NCH$_2$Ar), 7.30–7.37 (m, 3H, ArH), 7.48 (d, J=8.78 Hz, 1H, ArH), 7.78 (s, 1H, ArH); 7.84 (dd, J=6.59, 2.20 Hz, 1H, ArH), 8.06 (s, 1H, ArH), 8.29 (s, 1H, ArH).
MS(APCI+): m/z 408.2 (MH$^+$).

Example 33

3-(3,4-Difluoro-benzyl)-1-methyl-6-(3-[1,2,4] triazol-1-yl-prop-1-ynyl)-1H-quinazoline-2,4-dione The compound is obtained according to the procedure of Example 25, Step 2, but using 1-prop-2-ynyl-1H-[1,2,4] triazole.
Weight: 0.25 g Yield=88%
MP: 185–187° C.
Anal. Calcd for C$_{21}$H$_{15}$N$_5$O$_2$F$_2$: C, 59.4; H, 4.10; N, 16.3. Found: C, 59.7; H, 3.75; N, 16.1
N.M.R: DMSO $^1$H δ (ppm): 3.54 (s, 3H, NCH$_3$), 5.07 (s, 2H, CCH$_2$Ar), 5.41 (s, 2H, NCH$_2$Ar), 7.32–7.35 (m, 3H, ArH), 7.47 (d, J=8.54 Hz, 1H, ArH), 7.85 (dd, J=8.78, 2.20 Hz, 1H, ArH); 8.02–8.05 (m, 2H, ArH), 8.67 (s, 1H, Ar).
Ms(APCI+): m/z 408.1 (MH$^+$).

Example 34

3-(3,4-Dichloro-benzyl)-1-methyl-6-(3-[1,2,4] triazol-1-yl-prop-1-ynyl)-1H-quinazoline-2,4-dione The compound is obtained according to the procedure of Example 25, Step 2, but using 1-prop-2-ynyl-1H-[1,2,4] triazole.
Weight: 0.20 g Yield=71%
MP: 171–172° C.
Anal. Calcd for C$_{21}$H$_{15}$N$_5$O$_2$Cl$_2$: C, 55.6; H, 3.75; N, 15.3. Found: C, 55.7; H, 3.56; N, 14.9
N.M.R: DMSO $^1$H δ (ppm): 3.51 (s, 3H, NCH$_3$), 5.08 (s, 2H, CCH$_2$Ar), 5.41 (s, 2H, NCH$_2$Ar), 7.29–7.32 (dd, J=8.54, 1.95 Hz, 1H, ArH), 7.48 (d, J=8.54 Hz, 1H, ArH), 7.54 (d, J=8.30 Hz, 1H, ArH), 7.59 (s, 1H, ArH), 7.84 (dd, J=8.54, 1.95 Hz, 1H), 8.03–8.06 (m, 2H, ArH), 8.67 (s, 1H, ArH),
MS(APCI+): m/z 441.1 (MH$^-$).

Example 35

3-(3,4-Dichloro-benzyl)-1-methyl-6-(3-phenyl-prop-1-ynyl)-1H-quinazoline-2,4-dione The compound is obtained according to the procedure of Example 25, Step 2, but using 3-phenyl-1-propyne.
Weight: 0.10 g Yield=34%
MP: 185–187° C.
HPLC=95.2% purity
N.M.R: DMSO $^1$H δ (ppm): 3.50 (s, 3H, NCH$_3$), 3.90 (s, 2H, CCH$_2$Ar), 5.09 (s, 2H, NCH$_2$Ar), 7.30–7.60 (m, 7H, ArH), 7.82 (dd, J=6.83, 1.95 Hz, 1H, ArH), 8.02 (d, J=2.20 Hz, 1H, ArH).
MS(APCI+): m/z 440.2 (MH$^+$).

Example 36

3-(4-Fluorobenzyl)-6-(3-phenyl-prop-1-ynyl)-1-methyl-1H-quinazolin-2,4-dione

Step 1: 2-amino-N-(4-fluorobenzyl)-5-iodo-benzainide
To a stirred solution of 6.15 g (38 mmol) 4-fluorobenzylamine hydrochloride and 3.84 g (38 mmol) triethylamine in 150 ml DMF are added successively 5.14 g (38 mmol) HOBT, 10 g (38 mmol) 2-amino-5-iodobenzoic acid and 7.29 g (38 mmol) EDAC at room temperature. After stirring overnight at this temperature, the solvent is removed under reduced pressure and the residue dissolved in dichloromethane. The organic phase obtained is washed successively with water, 1N hydrochloric solution and water, dried over sodium sulfate and concentrated to give the desired product as a solid:
Weight: 13.2 g Yield: 94%
Step 2: 3-(4-fluoro-benzyl)-6-iodo-1H-quinazolin-2,4-dione
To a solution of 13.2 g (35.6 mmol) of the compound obtained in Step 1 in 300 ml dry tetrahydrofurane are added 6.36 g (39.2 mmol) of 1,1'-carbonyldiimidazole. The mixture obtained is heated at 60° C. under stirring for 24 hours; 6.36 g of 1,1'-carbonyldiimidazole are added and the solution stirred and heated for further 24 hours. The solvent is evaporated under reduced pressure, the residue triturated in 500 ml water. Filter and dry to give a white solid.
Weight: 11.7 g Yield: 83%
Step 3: 3-(4-fluoro-benzyl)-6-iodo-1-methyl-1H-quinazolin-2,4-dione
To a stirred suspension of 11.7 g (29.5 mmol) of the compound obtained in Step 2 in 110 ml DMF were added 6.12 g (44.3 mmol) potassium carbonate and, 15 minutes later, 20.9 g (147 mmol) of iodomethane. The mixture is stirred at room temperature for 1.5 hour, the filtrate evaporated and the residue partitioned between water and dichloromethane. The organic phase is separated, washed with water, dried over sodium sulfate and concentrated to give the desired product as a white solid.
Weight: 12 g Yield: 99%
Step 4: 3-(4-Fluorobenzyl)-6-[3-phenyl-prop-1-ynyl]-1-methyl-1H-quinazolin-2,4-dione
To 0.5 g (1.21 mmol) of compound obtained in Step 3 and 0.625 g (4.84 mmol) of N-ethyl, N,N-di-isopropylamine in 5 ml of dimethylformamide are added bis-triphenylphosphine palladium dichloride (42 mg) followed by CuI (catalytic) under nitrogen atmosphere. 0.198 g (1.7 mmol) 3-phenyl-prop-1-yne is added and the mixture is heated to 50° C. for 1.5 hour. The mixture is allowed to cool, water added and the mixture obtained stirred for 30 minutes. Filter and dry to give 0.58 g of crude solid. Purify by chromatography (dichloromethane 70/cyclohexane 30 eluent).
Weight: 0.37 g Yield: 77%
Sample recrystallized in methanol
N.M.R: CDCl$_3$ $^1$H δ (ppm):; 3.57 (s, 3H); 3.84 (s, 2H); 5.22 (s, 2H); 6.92–7.02 (m, 2H); 7.11 (d, 1H); 7.27 (d, 1H); 7.31–7.44 (m, 4H); 7.47–7.56 (m, 2H); 7.69 (d, 1H); 8.30 (s, 1H).
MP=160° C.
Purity (HPLC): 99%

Example 37

3-(4-Fluorobenzyl)-6-[3-(4-methoxyphenyl)-prop-1-ynyl]-1-methyl-1H-quinazolin-2,4-dione The compound is obtained according to the procedure of Example 36 from Step 1 to Step 4, but using 3-(4- methoxyphenyl)-prop-1-yne (described in the literature: *J. Prakt. Chem.*, 1966, 33, 84–95) in Step 4 instead 3-phenyl-prop-1-yne
Sample recrystallized in methanol
Yield: 25%
N.M.R: CDCl$_3$ $^1$H δ (ppm): 3.58 (s, 3H); 3.77 (s, 2H); 3.81 (s, 2H); 5.22 (s, 2H); 6.89 (d, 2H); 6.94–7.01 (m, 2H); 7.11 (d, 1H); 7.31 (d, 2H); 7.49–7.54 (m, 2H); 7.68 (d, 1H); 8.29 (s, 1H).
MP=136° C.
Purity (HPLC): 98%

Example 38

3-(4-Fluorobenzyl)-6-[3-(4-methoxyphenyl)-3-oxo-prop-1-ynyl)-1-methyl-1H-quinazolin-2,4-dione Step 1: 3-(4-Fluorobenzyl)-6-[2-trimethylsilyl-ethyn-1-yl]-1-methyl-1H-quinazolin-2,4-dione To a stirred solution of 2.0 g (4.87 mmol) of the compound prepared according to the procedure of Example 36 Step 3 and 2.52 g (4.84 mmol) of N-ethyl, N,N-di-isopropylamine in 20 ml of dimethylformamide is added bis-triphenylphosphine palladium dichloride (170 mg, catalytic) followed by CuI (catalytic) under nitrogen atmosphere. 0.67 g (6.8 mmol) of 2-trimethylsilylacetylene is added and the mixture is stirred at room temperature for 1.5 hour. The mixture is allowed to cool, water added and the mixture obtained stirred for 30 minutes. Filter and dry to give the crude product.
Weight: 1.8 g Yield: 97%

Step 2: 3-(4-Fluorobenzyl)-6-(ethyn-1-yl)-1-methyl-1H-quinazolin-2,4-dione

To a stirred solution of 0.5 g (1.31 mmol) of the compound obtained in Step 1 in 200 ml methanol is added 1.44 ml 1M NaOH solution. The mixture is stirred at room temperature for 2 hours, the insoluble solid filtered off and the filtrate concentrated under vacuum; the residue is partitioned between water and dichloromethane, the organic phase is separated, washed with water, dried over sodium sulfate and concentrated to give the desired product as a white solid.
Weight: 0.4 g Yield: 100%

Step 3: 3-(4-Fluorobenzyl)-6-[3-(4-methoxyphenyl)-3-oxo-propyn-1-yl]-1-methyl-1H-quinazolin-2,4-dione To a solution of 0.3 g (0.97 mmol) of the compound obtained in Step 2 and 0.39 g (3.88 mmol) of triethylamine in 5 ml of benzene are added successively 34 mg (catalytic) of bis-triphenylphosphine palladium dichloride and 0.23 g (1.36 mmol) of 4-methdxybenzoyl chloride. The mixture is heated at 70° C. under stirring for 1.5 hour, allowed to cool and partitioned between water and dichloromethane. The organic phase is separated, washed with brine, dried over sodium sulfate and concentrated to give the crude product as 0.45 g of white solid. Purify by chromatography (dichloromethane eluent):
Weight: 0.2 g Yield: 46%
N.M.R: CDCl$_3$ $^1$H δ (ppm): 3.61 (s, 3H); 3.91 (s, 3H); 5.24 (s, 2H); 6.93–7.03 (m, 3H); 7.21–7.28 (m, 2H); (d, 1H); 7.49–7.57 (m, 2H); 7.92 (d, 1H); 8.18 (d, 2H); 8.54 (s, 1H).
MP=240° C.
Purity (HPLC)=96%

Pharmacological Studies of Compounds of the Invention

Example 39

Evaluation of the in vitro Activity of the MMP-13 Inhibitor Compounds According to the Invention The inhibitory activity of the compounds of formula (I) according to the invention with respect to matrix metalloprotease-13 is evaluated by testing the ability of the compounds of the invention to inhibit the proteolysis of a peptide substrate with MMP-13.

The peptide substrate used in the test is the following peptide: Ac-Pro-Leu-Gly-thioester-Leu-Leu-Gly-OEt.

The inhibitory activity of a compound of formula (I) according to the invention is expressed as the IC$_{50}$ value, which is the concentration of inhibitor for which an inhibition of 50% of the activity of the matrix metalloprotease under consideration is observed.

To carry out this test, a reaction medium of 100 μl volume is prepared, containing: 50 mM of HEPES buffer, 10 mM of CaCl$_2$ and 1 mM of 5,5'-dithiobis-(2-nitrobenzoic acid) (DTNB), and 100 μM of substrate, the pH being adjusted to 7.0. Increasing concentrations of the inhibitory compound present in a 2.0% DMSO solution and 2.5 nM of the catalytic domain of human MMP-13 are added to the test samples. The concentrations of inhibitors present in the test samples range from 100 μM to 0.5 nM. The measurement of the proteolysis of the substrate peptide is monitored by measuring the absorbence at 405 nm using a spectrophotometer for reading microplates, at the laboratory temperature, the measurements being carried out continuously for 10 to 15 minutes. The IC$_{50}$ values are calculated from a curve in which the percentage of the catalytic activity relative to the control is represented on the X-axis and the concentration of inhibitor is represented on the Y-axis. The IC$_{50}$ values on MMP-13 of the compounds of Examples 1 to 38 are all below 10 μM.

The test described above for the inhibition of MMP-13 was also adapted and used to determine the ability of the compounds of formula (I) to inhibit the matrix metalloproteases MMP-1, MMP-2, MMP-3, MMP-7, MMP-9, MMP-12 and MMP-14. The results obtained show that the compounds according to the invention generally have IC$_{50}$ values for MMP-13 which are about 100 times lower than the IC$_{50}$ values for the same compounds with respect to the other matrix metalloproteases tested.

What is claimed is:

1. A compound selected from those of formula (I):

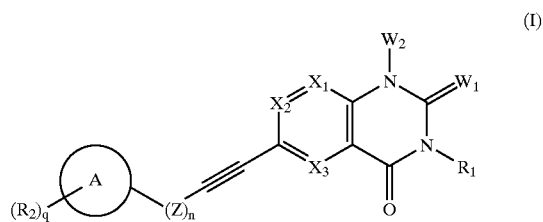

wherein
W$_1$ represents an oxygen atom, a sulfur atom, or a —NR$_3$ group in which R$_3$ represents hydrogen atom, (C$_1$–C$_6$) alkyl, hydroxyl or cyano,
W$_2$ represents a group selected from:
hydrogen atom, trifluoromethyl, amino, mono(C$_1$–C$_6$) alkylamino, di(C$_1$–C$_6$)alkylamino,
(C$_1$–C$_6$)alkyl, (C$_2$–C$_6$)alkenyl, (C$_2$–C$_6$)alkynyl, aryl, aryl(C$_1$–C$_6$)alkyl, cycloakyl(C$_1$–C$_6$)alkyl, 5- or 6-membered monocycle heteroaryl, and 5- or 6-membered monocycle heterocycloalkyl, each of these groups being optionally substituted by one to four groups, which may be identical or different independently of each other, selected from halogen, amino, mono(C$_1$–C$_6$)alkylamino, di(C$_1$–C$_6$) alkylamino, cyano, trihalogeno(C$_1$–C$_6$)alkyl, ($C_1$–$C_7$)acyl, —C(=O)O$R_4$, —O$R_4$ and —S$R_4$, wherein $R_4$, represents a hydrogen atom or a ($C_1$–$C_6$) alkyl group, $X_1$, $X_2$ and $X_3$, identical or different independently of each other, represent a carbon atom, the said carbon atom being optionally substituted by one group selected from:
($C_1$–$C_6$)alkyl, hydroxyl, ($C_1$–$C_6$)alkoxy, halogen, trifluoromethyl, cyano, nitro,
—S(O)$_{n1}$$R_4$ wherein $n_1$ represents an integer from 0 to 2 inclusive and $R_4$ represents an hydrogen atom or a ($C_1$–$C_6$)alkyl group,
and —N$R_{10}$$R_{11}$, wherein:
$R_{10}$ and $R_{11}$, which may be identical or different independently of each other, represent a group selected from hydrogen, ($C_1$–$C_6$)alkyl, hydroxy ($C_1$–$C_6$)alkyl, and aryl($C_1$–$C_6$)alkyl,
or $R_{10}$ and $R_{11}$ form together with the nitrogen atom to which there are bound, a 5- or 6-ring members which can optionally contain a second hetero atom selected from nitrogen and oxygen, and which can be optionally substituted by a ($C_1$–$C_6$)alkyl group, n is an integer from 0 to 8 inclusive, Z represents —C$R_{12}$$R_{13}$, wherein $R_{12}$ and $R_{13}$, identical or different independently of each other, represent a group selected from hydrogen, ($C_1$–$C_6$)alkyl, trihalogeno($C_1$–$C_6$)alkyl, halogen, amino, mono($C_1$$C_6$)alkylamino, di($C_1$–$C_6$)alkylamino, —O$R_4$, —S$R_4$, —C(=O)O$R_4$, $R_4$ being as defined hereinbefore, or —C$R_{12}$$R_{13}$ form together a carbonyl group, and
wherein when n is greater than or equal to 2, the hydrocarbon chain Z optionally contains one or two isolated or conjugated multiple bonds,
and/or wherein when n is greater than or equal to 2 one of said —C$R_{12}$$R_{13}$ may be replaced with a group selected from oxygen, S(O)$_{n2}$ in which n2 represents an integer from 0 to 2 inclusive, —NH and —N($C_1$–$C_6$)alkyl, A represents a group selected from aryl, heteroaryl, cycloalkyl, and heterocycloalkyl, these groups being a 5- or 6-membered monocycle, or bicycle itself composed of two 5-or 6-membered monocycles, the groups $R_2$, which may be identical or different independently of each other, are selected from hydrogen, ($C_1$–$C_6$)alkyl, halogen, cyano, nitro, trihalogeno ($C_1$–$C_6$)alkyl, —N$R_{10}$$R_{11}$, —O$R_{14}$, —S$R_{14}$, —SO$R_{14}$, —SO$_2$$R_{14}$, ($C_1$–$C_7$)acyl, —(CH$_2$)$_k$N$R_{10}$$R_{11}$, —$X_5$(CH$_2$)$_k$N$R_{10}$$R_{11}$, —(CH$_2$)$_k$SO$_2$N$R_{14}$$R_{15}$, —$X_5$ (CH$_2$)$_k$C(=O)O$R_{14}$, —(CH$_2$)$_k$C(=O)O$R_{14}$, —$X_5$ (CH$_2$)$_k$C(=O)N$R_{14}$$R_{15}$, —(CH$_2$)$_k$C(=O)N$R_{14}$$R_{15}$, —$X_6$—$R_{16}$ and tri($C_1$–$C_5$)alkyl-Si—O— in which each alkyl is identical or different independently of each other, and in which:
$X_5$ represents an oxygen atom, a sulfur atom, a —NH group, or a —N($C_1$–$C_6$)alkyl group,
k is an integer from 0 to 3 inclusive,
$R_{10}$ and $R_{11}$ are as defined hereinbefore,
$R_{14}$ and $R_{15}$, identical or different independently of each other, represent hydrogen or ($C_1$–$C_6$)alkyl,
$X_6$ represents a single bond, —CH$_2$—, an oxygen atom or a sulfur atom which, is optionally substituted by one or two oxygen atoms,
$R_{16}$ represents a group selected from aryl, heteroaryl, heterocycloalkyl, and cycloalkyl, each of these groups being optionally substituted by one to four groups, which may be identical or different independently of each other, selected from ($C_1$–$C_6$)alkyl, halogen, trihalogeno($C_1$–$C_6$)alkyl, hydroxyl, ($C_1$–$C_6$)alkoxy, mercapto, ($C_1$–$C_6$)alkylthio, amino, mono($C_1$–$C_6$)alkylamino, and di($C_1$–$C_6$)alkylamino, q is an integer from 0 to 7 inclusive, $R_1$ represents hydrogen, ($C_1$–$C_6$)alkyl or the group of formula:

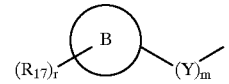

in which:
m is an integer from 0 to 3 inclusive,
Y represents —C$R_{18}$$R_{19}$, wherein $R_{18}$ and $R_{19}$ identical or different independently of each other, represent a group selected from hydrogen, ($C_1$–$C_6$)alkyl, and phenyl,
and wherein when m is greater than or equal to 2, the hydrocarbon chain Y optionally contains one multiple bond,
and/or wherein when in is greater than or equal to 2, one of said —C$R_{18}$$R_{19}$ may be replaced with a group selected from oxygen, —S(O)$_{n3}$ wherein n3 is an integer from 0 to 2 inclusive, and —NH—,
B represents a group selected from phenyl, pyridinyl, thienyl, imidazolyl, furyl, benzodioxolyl, beuzodioxinyl, benzothienyl, benzofuryl, benzo-1,2, 5-thiadiazolyl, benzo-1,2,5-oxadiazolyl, naphthyl and indolyl,
r is an integer from 0 to 3 inclusive,
the group(s) $R_{17}$ which may be identical or different, independently of each other, are selected from hydrogen, ($C_1$–$C_6$)alkyl, halogen, cyano, nitro, trihalogeno($C_1$–$C_6$)alkyl, —N$R_{14}$$R_{15}$, —O$R_{14}$, —SO$_2$$R_{14}$, —(CH$_2$)$_k$SO$_2$N$R_{14}$$R_{15}$, —$X_5$(CH$_2$)$_k$C (=O)O$R_{14}$, —(CH$_2$)$_k$C(=O)O$R_{14}$, —$X_5$(CH$_2$)$_k$C (=O)N$R_{14}$$R_{15}$, —(CH$_2$)$_k$C(=O)N$R_{14}$$R_{15}$ wherein:
k is an integer from 0 to 3 inclusive,
$X_5$ represents an oxygen atom, a sulfur atom, or a group —NH—,
$R_{14}$ and $R_{15}$, identical or different independently of each other, represent a hydrogen atom or a ($C_1$–$C_6$)alkyl group,
with the proviso that when $W_1$ represents —N$R_3$, $W_2$ represents hydrogen atom, $X_1$ and $X_2$ represent each a —CH group, $X_3$ represents nitrogen atom, n is equal to zero, A represents a phenyl group, q is equal to one, $R_1$ represents hydrogen atom, and $R_2$ represents a group —(CH$_2$)$_k$—CO$_2$$R_{14}$ bound on the para position of the phenyl ring, then k is an integer from 1 to 6,
and also with the proviso that compounds of formula (I) are not 2-amino-6-phenylethynyl-3H-pteridin-4-one,
and optionally, its optical isomers, N-oxides, and addition salts thereof with a pharmaceutically-acceptable acid or base,
it being understood that:
an aryl group denotes an aromatic monocycle or bicyclic system containing from 5 to 10 carbon atoms, and in the case of a bicyclic system, one of the ring of which is aromatic in character, and the other ring of which may be aromatic or partially hydrogenated;
a heteroaryl group denotes an aryl group as described above in which 1 to 4 carbon atoms are replaced by 1 to 4 hetero atoms selected from oxygen, sulfur and nitrogen;

a cycloalkyl group denotes a monocyclic or bicyclic system containing from 3 to 10 carbon atoms, this system being saturated or partially unsaturated but without aromatic character;

a heterocycloalkyl group denotes a cycloalkyl group as defined hereinbefore in which 1 to 4 carbon atoms are replaced by 1 to 4 hetero atoms selected from oxygen, sulfur, and nitrogen.

2. A compound according to claim 1, wherein:

$W_1$ represents an oxygen atom, a sulfur atom, or a —$NR_3$ group in which $R_3$ represents hydrogen atom, ($C_1$–$C_6$) alkyl, hydroxyl or cyano, $W_2$ represents a group selected from:
hydrogen atom, trifluoromethyl, amino, mono($C_1$–$C_6$) alkylamino, di($C_1$–$C_6$)alkylamino,
($C_1$–$C_6$)alkyl, ($C_2$–$C_6$)alkenyl, ($C_2$–$C_6$)alkynyl, aryl, aryl($C_1$–$C_6$)alkyl, cycloalkyl($C_1$–$C_6$)alkyl, 5- or 6-membered monocycle heteroaryl, and 5- or 6-membered monocycle heterocycloalkyl, each of these groups being optionally substituted by one to four groups, which may be identical or different independently of each other, selected from halogen, amino, mono($C_1$–$C_6$)alkylamino, di($C_1$–$C_6$) alkylamino, cyano, trihalogeno($C_1$–$C_6$)alkyl, ($C_1$–$C_7$)acyl, —C(=O)$OR_4$, —$OR_4$ and —$SR_4$, wherein $R_4$ represents a hydrogen atom or a ($C_1$–$C_6$) alkyl group, and $X_1$, $X_2$, $X_3$, $R_1$, $R_2$, A, Z, n and q are as defined in claim 1, optionally, its optical isomers, N-oxides, and addition salts thereof with a pharmaceutically-acceptable acid or base.

3. A compound according to claim 1 wherein:

$W_2$ represents a group selected from hydrogen atom, ($C_1$–$C_6$)alkyl, aryl($C_1$–$C_6$)alkyl and ($C_3$–$C_6$)cycloalkyl ($C_1$–$C_6$)alkyl, $W_1$ represents an oxygen atom or a sulfur atom, $X_1$ represents a —CH group, $X_2$ represents a —CH group or a nitrogen atom, $X_3$ represents a —CH group, and $R_1$, $R_2$, A, Z, n and q are as defined in claim 1, optionally, its optical isomers, N-oxides, and addition salts thereof with a pharmaceutically-acceptable acid or base.

4. A compound according to claim 1 wherein:

$W_2$ represents a group selected from hydrogen atom, amino, mono($C_1$–$C_6$)alkylamino, di($C_1$–$C_6$) alkylamino, ($C_1$–$C_6$)alkyl, ($C_2$–$C_6$)alkenyl, ($C_2$–$C_6$) alkynyl, aryl, aryl($C_1$–$C_6$)alkyl, and ($C_3$–$C_6$)cycloalkyl ($C_1$–$C_6$)alkyl, $W_1$ represents an oxygen atom or a sulfur atom, $X_1$ represents a nitrogen atom or a —CH group $X_2$ represents a —CH group, $X_3$ represents a —CH group, and $R_1$, $R_2$, A, Z, n and q are as defined in claim 1, optionally, its optical isomers, N-oxides, and addition salts thereof with a pharmaceutically-acceptable acid or base.

5. A compound according to claim 1 wherein:

$W_2$ represents a group ($C_1$–$C_6$)alkyl, $W_1$ represents an oxygen atom, $X_1$ represents a —CH group, $X_2$ represents a —CH group, $X_3$ represents a —CH group, and $R_1$, $R_2$, A, Z, n and q are as defined in claim 1, optionally, its optical isomers, N-oxides, and addition salts thereof with a pharmaceutically-acceptable acid or base.

6. A compound according to claim 1 wherein:

A represents a group selected from phenyl, pyridyl, thienyl, imidazolyl, furyl, benzodioxolyl, benzodioxinyl, benzothienyl, benzofuryl, benzo-1,2,5-thiadiazolyl, benzo-1,2,5-oxadiazolyl and indolyl, q is an integer from 0 to 4 inclusive, the group(s) $R_2$, which may be identical or different, are selected from hydrogen, ($C_1$–$C_6$)alkyl, halogen, cyano, nitro, trihalogeno($C_1$–$C_6$)alkyl, —$NR_{14}R_{15}$, —$OR_{14}$, —$SO_2R_{14}$, —$(CH_2)_kSO_2NR_{14}R_{15}$, —$X_5(CH_2)_kC(=O)OR_{14}$, —$(CH_2)_kC(=O)OR_{14}$, —$X_5(CH_2)_kC(=O)NR_{14}R_{15}$, —$(CH_2)_kC(=O)NR_{14}R_{15}$ and —$X_6$—$R_{16}$ in which:

$X_5$ represents an oxygen atom, a sulfur atom, or a —NH group, k is an integer from 0 and 3 inclusive, $R_{14}$ and $R_{15}$ identical or different, independently of each other, represent hydrogen or ($C_1$–$C_6$)alkyl, $X_6$ represents an oxygen atom, $R_{16}$ represents a phenyl group which is optionally substituted with one or more groups, which may be identical or different, independently of each other, selected from ($C_1$–$C_6$)alkyl, halogen, and hydroxyl, and $W_1$, $W_2$, $X_1$, $X_2$, $X_3$, $R_1$, Z and n are as defined in claim 1, optionally, its optical isomers, N-oxides, and addition salts thereof with a pharmaceutically-acceptable acid or base.

7. A compound according to claim 1 wherein:

A represents a group selected from phenyl, pyridinyl, thienyl, imidazolyl, furyl, and benzodioxolyl, q is an integer from 0 to 4 inclusive, the group(s) $R_2$, which may be identical or different, independently of each other, are selected from hydrogen, ($C_1$–$C_6$)alkyl, halogen, cyano, nitro, trihalogeno($C_1$–$C_6$)alkyl, —$NR_{14}R_{15}$, —$OR_{14}$, —$SO_2R_{14}$, —$(CH_2)_kSO_2NR_{14}R_{15}$, —$X_5(CH_2)_kC(=O)OR_{14}$, —$(CH_2)_kC(=O)OR_{14}$, —$X_5(CH_2)_kC(=O)NR_{14}R_{15}$, and —$(CH_2)_kC(=O)NR_{14}R_{15}$ in which:

$X_5$ represents an oxygen atom, a sulfur atom, or a —NH group, k is an integer from 0 and 3 inclusive, $R_{14}$ and $R_{15}$, identical or different, independently of each other, represent hydrogen or ($C_1$–$C_6$)alkyl, and $W_1$, $W_2$, $X_1$, $X_2$, $X_3$, $R_1$, Z and n are as defined in claim 1, optionally, its optical isomers, N-oxides, and addition salts thereof with a pharmaceutically-acceptable acid or base.

8. A compound according to claim 1 wherein:

A represents a group selected from phenyl, imidazolyl, 1H[1,2,3]triazolyl, and 1H[1,2,4]triazolyl, q is an integer from 0 to 2 inclusive, the group(s) $R_2$, which may be identical or different, independently of each other, are selected from hydrogen, —$OR_{14}$, —$X_6$—$R_{16}$, and tri($C_1$–$C_6$)alkyl-Si—O— in which each alkyl is identical or different independently of each other, in which:

$R_{14}$ represents hydrogen or ($C_1$–$C_6$)alkyl, $X_6$ represents a single bond, R$_{16}$ represents a phenyl group and W$_1$, W$_2$, X$_1$, X$_2$, X$_3$, R$_1$, Z and n are as defined in claim 1, optionally, its optical isomers, N-oxides, and addition salts thereof with a pharmaceutically-acceptable acid or base.

9. A compound according to claim 1 wherein n is equal to one, optionally, its optical isomers, N-oxides, and addition salts thereof with a pharmaceutically-acceptable acid or base.

10. A compound according to claim 1 wherein Z represents a group —CR$_{12}$R$_{13}$ in which R$_{12}$ and R$_{13}$ represent each a hydrogen atom, optionally, its optical isomers, N-oxides, and addition salts thereof with a pharmaceutically-acceptable acid or base.

11. A compound according to claim 1 wherein A represents a phenyl group or a 1-imidazolyl group optionally substituted by one group R$_2$ as defined in claim 1, optionally, its optical isomers, N-oxides, and addition salts thereof with a pharmaceutically-acceptable acid or base.

12. A compound according to claim 11 wherein A represents a phenyl group optionally substituted by one group R$_2$ as defined in claim 1, optionally, its optical isomers, N-oxides, and addition salts thereof with a pharmaceutically-acceptable acid or base.

13. A compound according to claim 11 wherein A, R$_2$ and q, took together, represent a para-methoxyphenyl group, optionally, its optical isomers, N-oxides, and addition salts thereof with a pharmaceutically-acceptable acid or base.

14. A compound according to claim 1 wherein:

R$_1$ represents a group of formula:

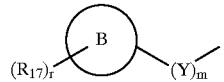

in which:
   m is an integer from 0 to 3 inclusive,
   Y represents —CR$_{18}$R$_{19}$, wherein R$_{18}$ and R$_{19}$, identical or different independently of each other, represent a group selected from hydrogen and methyl, and wherein when m is greater than or equal to 2, the hydrocarbon chain Y optionally contains one double bond,
   and/or wherein when m is greater than or equal to 2, one of said —CR$_{18}$R$_{19}$ may be replaced with a group selected from oxygen, —S(O)$_{n3}$ wherein n3 is an integer from 0 to 2 inclusive, and —NH—,
   B represents a group selected from phenyl, pyridinyl, thienyl, imidazolyl, furyl, and benzodioxolyl,
   r is an integer from 0 to 3 inclusive,
   the group(s) R$_{17}$ which may be identical or different, independently of each other, are selected from hydrogen, (C$_1$–C$_6$)alkyl, halogen, cyano, nitro, trihalogeno(C$_1$–C$_6$)alkyl, —NR$_{14}$R$_{15}$, —OR$_{14}$, —SO$_2$R$_{14}$, —(CH$_2$)$_k$SO$_2$NR$_{14}$R$_{15}$, —X$_5$(CH$_2$)$_k$C(=O)OR$_{14}$, (CH$_2$)$_k$C(=O)OR$_{14}$, —X$_5$(CH$_2$)$_k$C(=O)NR$_{14}$R$_{15}$, —(CH$_2$)$_k$C(=O)NR$_{14}$R$_{15}$ wherein:
      k is an integer from 0 to 3 inclusive,
      X$_5$ represents an oxygen atom, a sulfur atom, or a group —NH,
      R$_{14}$ and R$_{15}$, identical or different independently of each other, represent a hydrogen atom or a (C$_1$–C$_6$)alkyl group,
and W$_1$, W$_2$, X$_1$, X$_2$, X$_3$, R$_2$, Z, n and q are as defined in claim 1, optionally, its optical isomers, N-oxides, and addition salts thereof with a pharmaceutically-acceptable acid or base.

15. A compound according to claim 2 wherein W$_2$ represents an oxygen atom, W$_1$ represent a —NR$_3$ group in which R$_3$ represents a linear or branched (C$_1$–C$_6$)alkyl group and R$_1$ represent a group of formula:

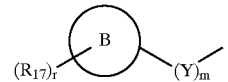

in which Y, B, R$_{17}$, m and r are as defined in claim 1, optionally, its optical isomers, N-oxides, and addition salts thereof with a pharmaceutically-acceptable acid or base.

16. A compound according to claim 15 wherein R$_1$ represent a group of formula:

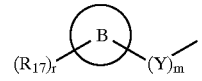

in which m is equal to one, Y represents a methylene group, B represents a phenyl group which is optionally substituted by one group R$_{17}$ which represents a group (CH$_2$)$_k$—C(=O)OR$_{14}$ in which k and R$_{14}$ are as defined in claim 1, optionally, its optical isomers, N-oxides, and addition salts thereof with a pharmaceutically-acceptable acid or base.

17. A compound according to claim 1, which is selected from:

methyl 4-{6-[3-(4-methoxyphenyl)-prop-1-ynyl]-1-methyl-2,4-dioxo-1,4-dihydro-2H-quinazolin-3-ylmethyl}-benzoate, 4-[1-methyl-2,4-dioxo-6-(3-phenyl-prop-1-ynyl)-1,4-dihydro-2H-quinazolin-3-ylmethyl]-benzoic acid, 4-{6-[3-(4-methoxy-phenyl)-prop-1-ynyl]-1-methyl-2,4-dioxo-1,4-dihydro-2H-quinazolin-3-ylmethyl}-benzoic acid, 4-(1-methyl-2,4-dioxo-6-(2-phenylethynyl)-1,4-dihydro-2H-quinazolin-3-ylmethyl)-benzoic acid, 3-(4-fluorobenzyl)-6-(3-phenyl-prop-1-ynyl)-1-methyl-1H-quinazolin-2,4-dione, 3-(4-fluorobenzyl)-6-[3-(4-methoxyphenyl)-3-oxo-prop-1-ynyl)-1-methyl-1H-quinazolin-2,4-dione, methyl 4-[1-methyl-2,4-dioxo-6-(3-phenyl-prop-1-ynyl)-1,4-dihydro-2H-quinazolin-3-ylmethyl]-benzoate, 3-(4-fluorobenzyl)-6-[3-(4-methoxyphenyl)-prop-1-ynyl]-1-methyl-1H-quinazolin-2,4-dione, 3-(3-chloro-benzyl)-1-methyl-6-(3-phenyl-prop-ynyl)-1H-quinazoline-2,4-dione, 3-(3-fluoro-benzyl)-1-methyl-6-(3-phenyl-prop-1-ynyl)-1H-quinazoline-2,4-dione, 3-(4-Chloro-benzyl)-1-methyl-6-(3-phenyl-prop-1-ynyl)-1H-quinazoline-2,4-dione, 3-(4-bromo-benzyl)-1-methyl-6-(3-phenyl-prop-1-ynyl)-1H-quinazoline-2,4-dione, 3-(3,4-difluoro-benzyl)-1-methyl-6-(3-phenyl-prop-1-ynyl)-1H-quinazoline-2,4-dione, tert-butyl 4-[6-(3-biphenyl-4-yl-prop-1-ynyl)-1-methyl-2,4-dioxo-1,4-dihydro-2H-quinazolin-3-ylmethyl]-benzoate, tert-butyl 4-{6-[3-(4-fluoro-phenyl)-prop-1-ynyl]-1-methyl-2,4-dioxo-1,4-dihydro-2H-quinazolin-3-ylmethyl}-benzoate, 4-[6-(3-imidazol-1-yl-prop-1-ynyl)-1-methyl-2,4-dioxo-1,4-dihydro-2H-quinazolin-3-ylmethyl]-benzoic acid-trifluoro-acetic acid, 3-(3,4-difluoro-benzyl)-6-(3-imidazol-1-yl-prop-1-ynyl)-1-methyl-1H-quinazoline-2,4-dione, 2-dimethylamino-ethyl 4-[1-methyl-2,4-dioxo-6-(3-phenyl-prop-1-ynyl)-1,4-dihydro-2H-quinazolin-3-ylmethyl]-benzoate, 4-(6-{3-[4-(tert-butyl-dimethyl-silanyloxy)-phenyl]-prop-1-ynyl}-1-methyl-2,4-dioxo-1,4-dihydro-2H-quinazolin-3-ylmethyl)-benzoic acid, N,N-dimethyl-4-[1-methyl-2,4-dioxo-6-(3-phenyl-prop-1-ynyl)-1,4-dihydro-2H-quinazolin-3-ylmethyl]-benzamide, 1-methyl-6-(3-phenyl-prop-1-ynyl)-3-[4-(piperidine-1-carbonyl)-benzyl]-1H-quinazoline-2,4-dione, N-ethyl-4-[1-methyl-2,4-dioxo-6-(3-phenyl-prop-1-ynyl)-1,4-dihydro-2H-quinazolin-3-ylmethyl]-benzamide, 6-[3-(4-chloro-phenyl)-prop-1-ynyl]-3-(3,4-difluoro-benzyl)-1-methyl-1H-quinazoline-2,4-dione, 3-(3-chloro-benzyl)-6-[3-(4-chloro-phenyl)-prop-1-ynyl]-1-methyl-1H-quinazoline-2,4-dione, 3-(4-hydroxymethyl-benzyl)-1-methyl-6-(3-phenyl-prop-1-ynyl)-1H-quinazoline-2,4-dione, 1-methyl-3-[4-(4-methyl-piperazine-1-carbonyl)-benzyl]-6-(3-phenyl-prop-1-ynyl)-1H-quinazoline-2,4-dione, N,N-bis-(2-hydroxy-ethyl)-4-[1-methyl-2,4-dioxo-6-(3-phenyl-prop-1-ynyl)-1,4-dihydro-2H-quinazolin-3-ylmethyl]-benzamide, 3-(3,4-difluoro-benzyl)-6-[3-(4-fluoro-phenyl)-prop-1-ynyl]-1-methyl-1H-quinazoline-2,4-dione, 3-(3,4-difluoro-benzyl)-1-methyl-6-(3-[1,2,3]triazol-1-yl-prop-1-ynyl)-1H-quinazoline-2,4-dione, 3-(3,4-difluoro-benzyl)-1-methyl-6-(3-[1,2,4]triazol-1-yl-prop-1-ynyl)-1H-quinazoline-2,4-dione, 3-(3,4-dichloro-benzyl)-1-methyl-6-(3-[1,2,4]triazol-1-yl-prop-1-ynyl)-1H-quinazoline-2,4-dione, and 3-(3,4-dichloro-benzyl)-1-methyl-6-(3-phenyl-prop-1-ynyl)-1H-quinazoline-2,4-dione.

18. A pharmaceutical composition comprising as active ingredient an effective amount of a compound as claimed in claim 1, alone or in combination with one or more pharmaceutically-acceptable carrier or excipient.

19. A method for treating a living body afflicted with a disease that is mediated by a matrix metalloproteinase-13 enzyme, comprising the step of admistering to the living body an amount of a compound of claim 1, or a pharmaceutically aeceptable salt thereof, which is effective for treatment of the disease, wherein the disease is rheumatoid arthritis.

* * * * *